US010902714B2

(12) United States Patent
Bergman et al.

(10) Patent No.: US 10,902,714 B2
(45) Date of Patent: Jan. 26, 2021

(54) SYSTEMS AND METHODS FOR REDUCING ADVERSE HEALTH EVENTS IN FIRST RESPONDERS

(71) Applicants: Coho Industries LLC, Hillsboro, OR (US); Pacific University, Forest Grove, OR (US)

(72) Inventors: Aaron Leslie Bergman, Hillsboro, OR (US); Mark K. Leavitt, North Plains, OR (US); Juan Andres Soria, Hillsboro, OR (US); Joshua Benjamin Kaplan, Portland, OR (US); Eli Malachy Dunn Dapolonia, Portland, OR (US); Kaylie Ann Green, Marysville, WA (US)

(73) Assignees: COHO INDUSTRIES LLC, Hillsboro, OR (US); PACIFIC UNIVERSITY, Forest Grove, OR (US)

( * ) Notice: Subject to any disclaimer, the term of this patent is extended or adjusted under 35 U.S.C. 154(b) by 0 days.

(21) Appl. No.: 16/276,484

(22) Filed: Feb. 14, 2019

(65) Prior Publication Data

US 2020/0265700 A1    Aug. 20, 2020

(51) Int. Cl.

| G08B 1/08 | (2006.01) |
|---|---|
| G08B 21/04 | (2006.01) |
| G16H 50/30 | (2018.01) |
| G08B 5/36 | (2006.01) |
| G08B 25/01 | (2006.01) |
| G08B 21/18 | (2006.01) |

(52) U.S. Cl.
CPC .......... G08B 21/0453 (2013.01); G08B 5/36 (2013.01); G08B 21/182 (2013.01); G08B 25/016 (2013.01); G16H 50/30 (2018.01)

(58) Field of Classification Search
CPC .... G08B 21/0453; G08B 21/182; G08B 5/36; G08B 25/016; G16H 50/30
USPC ...................................... 340/539.12
See application file for complete search history.

(56) References Cited

U.S. PATENT DOCUMENTS

| 5,684,455 A | 11/1997 | Williams et al. |
|---|---|---|
| 6,199,550 B1 | 3/2001 | Wiesmann et al. |
| 6,957,166 B1 | 10/2005 | Howie et al. |
| 7,135,960 B2 | 11/2006 | Arcaria et al. |
| 7,336,187 B2 | 2/2008 | Hubbard, Jr. et al. |

(Continued)

FOREIGN PATENT DOCUMENTS

| CN | 203468597 U | 3/2014 |
|---|---|---|
| CN | 203552406 U | 4/2014 |

(Continued)

*Primary Examiner* — Tanmay K Shah
(74) *Attorney, Agent, or Firm* — McCoy Russell LLP

(57) ABSTRACT

Methods and systems are provided for an alert system for reducing a risk of an adverse health event in a firefighter or first responder. In one example, the alert system may comprise a wearable sensor and an alerting device, where the alerting device may be operable to receive physiological and/or environmental data from the wearable sensor and where the alerting device may be further operable to issue an alert based on the received physiological and/or environmental data. In some examples, the alert may be a function of one or more personalized thresholds for evaluating a stress level of the firefighter or first responder. In some examples, the alert may be issued via multiple communication channels.

28 Claims, 28 Drawing Sheets

(56) References Cited

U.S. PATENT DOCUMENTS

| | | |
|---|---|---|
| 7,378,954 B2 | 5/2008 | Wendt |
| 7,880,607 B2 | 2/2011 | Olson et al. |
| 8,085,144 B2 | 12/2011 | Appelt et al. |
| 10,003,945 B2 | 6/2018 | Papakonstantinou et al. |
| 2006/0252999 A1 | 11/2006 | Devaul et al. |
| 2008/0146895 A1* | 6/2008 | Olson ................ G08B 21/0453 |
| | | 600/301 |
| 2010/0298683 A1 | 11/2010 | Cabrera et al. |
| 2011/0140913 A1 | 6/2011 | Montenero |
| 2014/0038668 A1* | 2/2014 | Vasavada ............... H04M 11/04 |
| | | 455/556.1 |
| 2015/0382198 A1* | 12/2015 | Kashef ................... H04L 63/08 |
| | | 726/5 |
| 2017/0181255 A1* | 6/2017 | Jeremy ............. H05B 37/0272 |
| 2019/0206233 A1* | 7/2019 | Huseth .................. G08B 25/10 |

FOREIGN PATENT DOCUMENTS

| | | |
|---|---|---|
| CN | 203789907 U | 8/2014 |
| CN | 104305984 B | 6/2016 |
| CN | 107085920 A | 8/2017 |

* cited by examiner

SYSTEMS AND METHODS FOR REDUCING ADVERSE HEALTH EVENTS IN FIRST RESPONDERS

FIELD OF THE INVENTION

The present invention pertains generally to reducing a risk of adverse health events such as cardiac arrest in persons including first responders and/or firefighters, by means of alerts that are based at least in part on physiological parameters. The alerts are provided via multiple channels, and are tailored to specific situations and/or personalized thresholds.

BACKGROUND OF THE INVENTION

Sudden cardiac death (SCD) is the primary reason for on-the-job fatality of firefighters and first responders of all ages. For such persons, adverse cardiac events may involve a combination of personal and work-related factors. Personal factors may include age, gender, family history, diabetes, hypertension, smoking, cholesterol levels, physical fitness levels, etc. Occupational factors may include exposure to smoke, heavy physical exertion, heat stress, and exposure to carbon monoxide, among others. As an example, during fire suppression activities, a combination of heat stress, smoke, intense physical exertion, critical incident stress and organizational stress can raise a firefighter's cardiovascular stress to dangerous levels. Importantly, elevated stress levels may persist for some amount of time after the actual activity of fire suppression has stopped, where the particular amount of time may be a function of at least the personal factors discussed above.

Current and past approaches taken to address such issues include strategies directed to medical evaluation programs, comprehensive wellness and physical fitness programs, equipment use training, and job-site management training to reduce hazardous exposures and heat stress. For example, medical evaluation programs may include ensuring that physicians conducting such medical evaluations are knowledgeable about the physical demands of firefighting, the essential tasks, and consensus guidelines developed for firefighters. Wellness/fitness programs may be specifically implemented to reduce risk factors related to cardiovascular disease and to improve cardiovascular capacity. Exposure to carbon monoxide and other fire contaminants may be minimized through proper training in management of a fire scene and proper use of respiratory protection. Adequate staffing levels may be utilized to prevent over-exertion.

However, such strategies have largely failed to reduce the incidence of SCD among firefighters and/or first responders. Part of this failure may be attributable to firefighter/first responder culture, in which such individuals may often choose to work through pain and/or discomfort, and avoid asking for help even in situations of significant distress. Accordingly, additional solutions are desirable to significantly lower the risk of incidence of SCD among firefighters and/or first responders.

Towards this end, U.S. Pat. No. 8,085,144 (Appelt et al., hereinafter Appelt) discloses a system and method for identifying, monitoring, and evaluating hazardous or potentially hazardous conditions. Specifically, the system includes a sensor in communication with indicator lights, both of which are integrated into a safety helmet, face shield, or facemask of a firefighter/first responder. In another example, U.S. Pat. No. 6,199,550 (Wiesmann et al., hereinafter Wiesmann) discloses a self-contained breathing apparatus (SCBA) that includes a series of physiologic and environmental sensors. The sensors communicate with individual display units attached to a shield or the mask of the SCBA to indicate safety levels associated with data from the sensors.

However, the inventors herein have recognized potential problems with the above-mentioned solutions. For example, the sensor systems of Appelt and Wiesmann are associated with a safety helmet, face shield and/or facemask of a firefighter/first responder. However, a large number of SCD and other cardiovascular disease events may occur post-strenuous emergency duty and/or during the course of other job-related duties where the safety helmet/facemask has been removed. Given team dynamics associated with firefighting, any such on-duty adverse health events may jeopardize job performance and safety of co-workers as well as the affected individual, and may compromise public safety.

Thus, the systems and methods disclosed with regard to Appelt and Wiesmann do not allow for monitoring individual personnel at times when the safety helmet/facemask has been removed, and therefore do not disclose methodology for alerting such individuals of potential adverse health events and for taking mitigating action during such times. Furthermore, given that placement of the indicator lights is disclosed as being associated with the safety helmet/facemask, it may be challenging and/or inconvenient for nearby firefighters and/or first responders to regularly check to see whether a fellow firefighter/first responder is in need of some level of mitigating action. For example, during the course of duty-related activity where safety helmets/facemasks are being worn by individual firefighters, taking time to look directly at a face of a fellow firefighter in order to assess whether that individual is experiencing an elevated level of stress may be a distraction, and may take focus away from other potentially dangerous situations that require a high-level of engagement.

In still another example, indicator lights associated with a safety helmet/facemask of one particular individual may not be effective in terms of being able to alert a nearby firefighter/first responder in a common case where there is an abundance of smoke in the area in which the firefighters/first responders are operating. More specifically, any lights associated with the safety helmet/facemask of a particular individual that are capable of conveying information to both the individual and other nearby individuals must not be so bright that they impact the ability of the individual wearing the mask to effectively see. However by limiting the brightness, the ability of such lights to also alert nearby individuals may be degraded in situations of low visibility due to smoke.

Thus, there is a need for systems and methods which may enable effective monitoring and means of alerting one or more firefighters and/or first responders of adverse health events both while on emergency duty-related activities, as well as during a time period encompassing post emergency duty-related activities and/or during other non-emergency duties and tasks. Additionally, there is a need for systems and methods which readily enable firefighters/first responders engaging in complex tasks to identify whether another fellow firefighter/first responder is in need of attention in such a way that is not distracting, is readily interpretable, and is effective even in situations of very low visibility which may occur in smoke-filled buildings in which firefighters/first responders regularly operate. Still further, there is a need for systems and methods which may alert firefighters in a fashion which does not require firefighters/first responders to pay attention to their devices, such that they may be passively apprised of a risk event.

SUMMARY OF THE INVENTION

Discussed herein, systems and methods for reducing a risk of adverse health events (e.g. sudden cardiac death) in firefighters and/or first responders are provided to address the above-mentioned issues. Specifically, systems and methods are provided for monitoring physiological and/or environmental parameters in first responders, where said systems and methods issue alerts at multiple levels and through multiple channels to provide redundancy and reliability of the alerts in challenging environments such as those generally experienced by firefighters and/or first responders. Specifically, the monitoring of physiological and/or environmental parameters may be via a wearable sensor. Discussed herein, physiological and/or environmental parameters may be referred to as sensor data. For example, sensor data may comprise physiological parameters recorded by the wearable sensor. Sensor data may in other examples comprise environmental parameters recorded by the wearable sensor. In other examples, sensor data may comprise some combination of physiological and environmental parameters recorded by the wearable sensor. The wearable sensor may communicate such physiological and/or environmental parameters to an alerting device. The alerting device may be configured with preset personalized thresholds related to the physiological and/or environmental parameters, such that alerts provided may be specific to a particular individual wearing the alerting device. The personalized thresholds may be communicated to the alerting device via a stress management application (e.g. software application), also referred to herein as a stress management application. The personalized thresholds may be set, for example, via an administrator via input into the stress management application and/or may be set/updated through the stress management application via output from an analytics module that processes data acquired from the wearable sensor. In some examples the personalized thresholds may pertain to individuals. In other examples, the personalized thresholds may pertain to groups of individuals.

The issuing of alerts via multiple levels and through multiple channels may include issuing a visual alert capable of being visualized by a wearer of the alerting device and wearable sensor and/or by nearby firefighters/first responders, issuing an audible alert that stems from a device worn by the wearer of the alerting device and/or is transmitted across a portable radio network, and/or transmitting the alert to a remote location (e.g. to a mobile data terminal used by an incident commander) in the form of a text message, email, update to the stress management application described above, etc. The visual alert may comprise use of signal light(s) for which a color of light projected may reflect an intensity of a current stress level the wearer of the alerting device is experiencing, and where a sequence pattern associated with the projected light reflects a duration of time that the wearer of the alerting device has been experiencing a particular stress level.

In one example, the alerting device comprises an adapter or adapter module that communicably couples an existing portable radio to an existing remote speaker/microphone. In another example, the alerting device may replace the existing remote speaker/microphone. In either example, power for the alerting device may be provided via harvesting power from the portable radio via a radio interface connector (discussed in further detail below).

In this way, by implementing systems and methods that encompass the above-discussed capabilities, risk of adverse health events in firefighters and/or first responders may be reduced.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION OF THE INVENTION

The following description relates to systems and methods for an alert system for reducing adverse health events in firefighters and/or first responders. Alerts (e.g. visual, audible) indicating potential adverse health events may be generated via an alerting device based on data including physiological and/or environmental parameters collected via a wearable sensor. The alerting device may receive and transmit the data to a stress management application.

Figure 1:
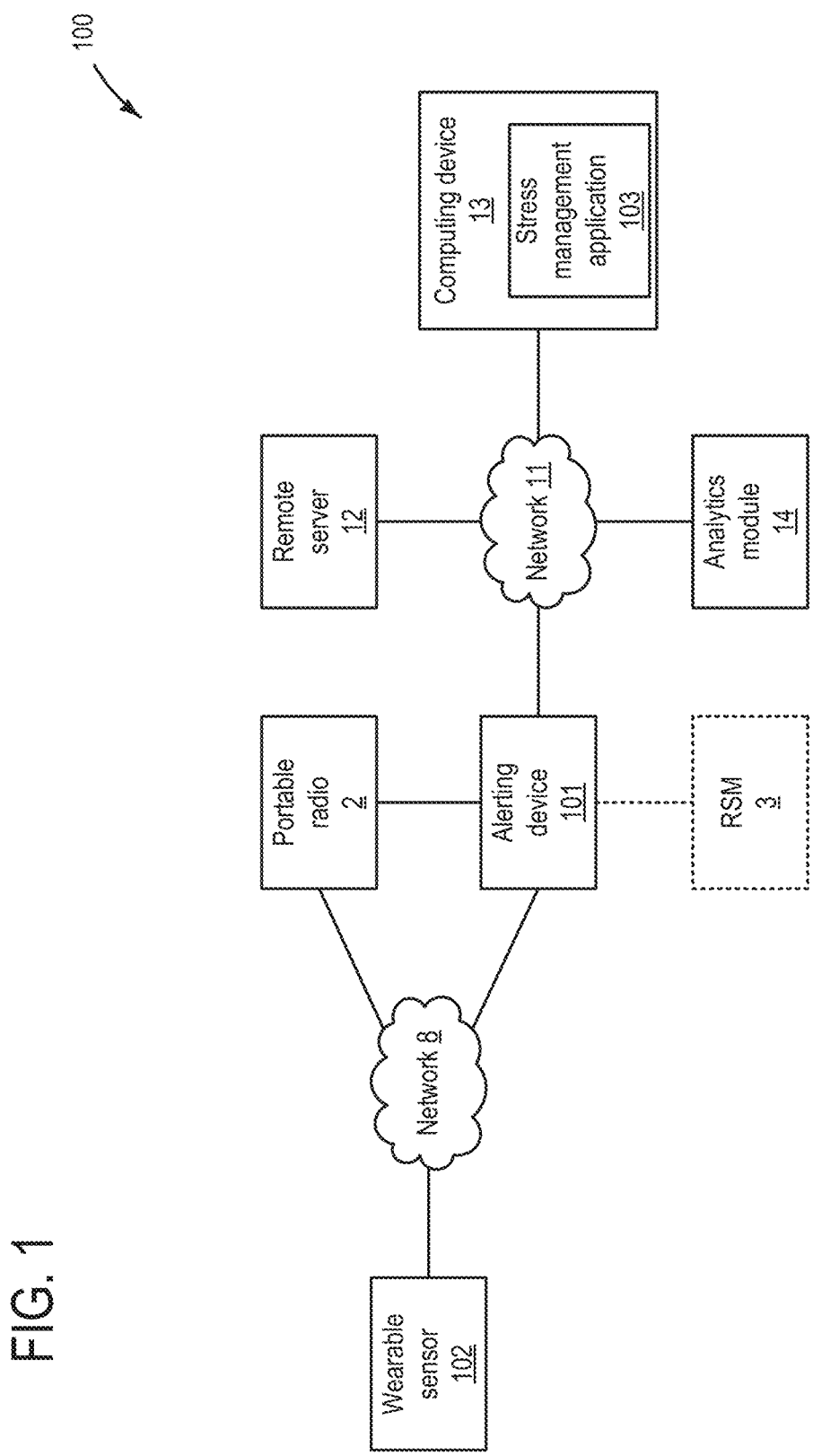
FIG. 1 depicts a schematic diagram of an alerting system of the present disclosure.

FIG. 1 is an example schematic diagram of an alerting, or alert, system 100 for monitoring a level of physiological and/or environmental stress of a firefighter or first responder (not shown at FIG. 1) and issuing visual and/or audible alerts, or alert signals, based on said monitoring. A wearable sensor 102 may monitor, record, and transmit data related to one or more physiological and/or environmental parameters. Wearable sensor 102 may be wirelessly coupled (e.g. via Bluetooth technology) via short-range radio network 8 to an alerting device 101, wherein alerting device 101 may be operable to receive the data. Alerting device 101 may be wired to, directly coupled with, or be in wireless communication (e.g. via short-range network 8) with a portable radio 2. Portable radio 2 may be in communication with one or more other portable radios (not shown) associated with one or more other firefighters or first responders, or with a base station. In some examples, portable radio 2, via alerting device 101, may be in communication with a remote speaker/microphone (RSM) 3. In other examples, alerting device 101 may include capabilities of RSM 3, such that RSM 3 may be optional (accordingly, RSM 3 is differentiated in FIG. 1 from other components of alerting system 100 as a dashed box).

A wireless communications device (e.g. cellular radio transceiver; not shown but see below) may be included in alerting device 101 such that alerting device 101 may communicate the data collected by wearable sensor 102 across network 11 (e.g. cellular network, or in other words longer-range radio than network 8), to one or more remote storage devices, such as a remote server 12, a computing device 13, and/or an analytics module 14. Therefrom, in some examples, the data may be transmitted to remote server 12, such as a cloud-based server, for storage of said data. While depicted as different networks, it may be understood that in some examples network 11 and network 8 may comprise the same network. Computing device 13 (e.g. mobile data terminal, laptop, smartphone, tablet, desktop computer, etc.) may enable retrieval of data stored at remote server 12 via stress management application, or alternately referred to herein as stress management application, 103 stored on computing device 13, such that said data stored at remote server may be made available to a user, such as an incident commander. Stress management application 103 may enable such a user to browse, search, process/manipulate, analyze, etc., said data. Stress management application 103 may further enable such a user to set one or more parameters, settings, personalized thresholds, etc., associated with alerting device 101, as will be discussed in greater detail below.

Analytics module 14 may be in further communication with network 11 (e.g. cellular network), such that analytics module 14 may receive data from other components of alerting system 100 (such as remote server 12) and may transmit data to the other components of alerting system 100 (such as stress management application 103 on computing device 13). In one example, analytics module 14, through machine, or deep, learning, may determine personalized, or individualized, thresholds based upon the data collected by wearable sensor 102 for evaluating the level of physiological and/or environmental stress of the firefighter or first responder. In this way, alerting system 100 may account for dynamically changing stress levels by analyzing changes in physiological and/or environmental parameters as recorded by wearable sensor 102. Further, alerting system 100 may be operable to notify the firefighter or first responder, the one or more other firefighters or first responders, the incident commander, and/or other individuals assisting in a firefighting or first response engagement of a potential adverse health event for the firefighter or first responder via issued alerts based on the personalized thresholds along multiple, redundant communication channels (e.g. the issued alerts may be visual or audible, or may be broadcast via short-range network 8 and/or network 11).

Figure 2A:
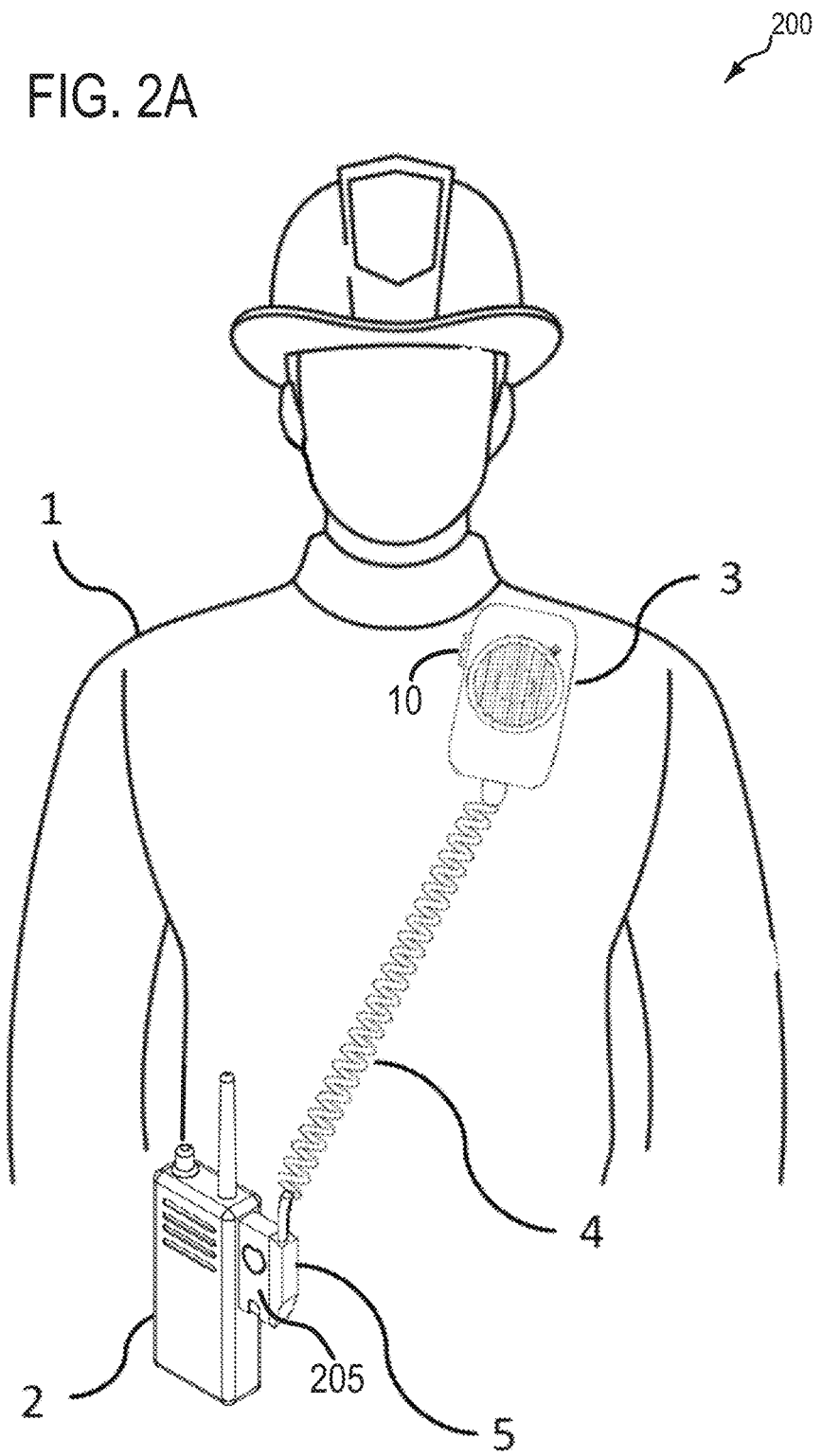
FIG. 2A depicts an example illustration of a first responder wearing a portable radio coupled via an adapter module to a remote speaker/microphone (RSM).

Turning to FIG. 2A an example depiction 200 of a firefighter or first responder 1, is shown. A firefighter or first responder may utilize a wide variety of appropriate protective equipment for a given situation. Such equipment may include boots, gloves, a coat and/or other clothing that may enable protection against fire and heat. Another piece of equipment common to firefighters and first responders is a self-contained breathing apparatus (SCBA) which may provide breathable air in an immediately dangerous to life or health (IDLH) atmosphere. Such components discussed above are not shown at FIG. 2A for clarity. Instead, depicted at FIG. 2A is firefighter or first responder 1, wearing a belt-mounted portable radio 2. In some examples, said radio 2 may be communicatively coupled with a shoulder-worn RSM 3 via an adapter 205 or adapter module 205 (as discussed in greater detail below), adapter 205 comprising one embodiment of the alerting device (e.g. 101) as discussed herein. RSM 3 may allow firefighter or first responder 1 to talk and listen without having to remove belt-mounted portable radio 2 from belts and/or carrying cases. As an example, RSM 3 may include a push-to-talk (PTT) actuator 10 for enabling firefighter or first responder 1 to speak into RSM 3. It may be understood that PTT actuator 210 may comprise a button that can be depressed, a slidable actuator, etc. RSM 3 may clip onto clothing (e.g. coat, lapel, jacket, etc.) for convenient use. RSM 3 may connect to portable radio 2 via adapter 205 via retractile cable 4 and RSM connector 5, although in other examples RSM 3 may wirelessly couple to portable radio 2 and adapter 205. For example, portable radio 2 may in some examples be electronically coupled to an adapter dongle (not shown, where the adapter dongle replaces RSM connector 5) via adapter 205, enabling RSM 3 to wirelessly couple to portable radio 2 (e.g. via Bluetooth technology) and adapter 205, without departing from the scope of this disclosure. As mentioned above, it may be understood that adapter 205 comprises one embodiment of the alerting device of the present disclosure, and that where adapter 205 is not included, RSM 3 simply is communicatively coupled (e.g. via wired or wireless communication) to portable radio 2, without inclusion of adapter 205.

Figure 2B:
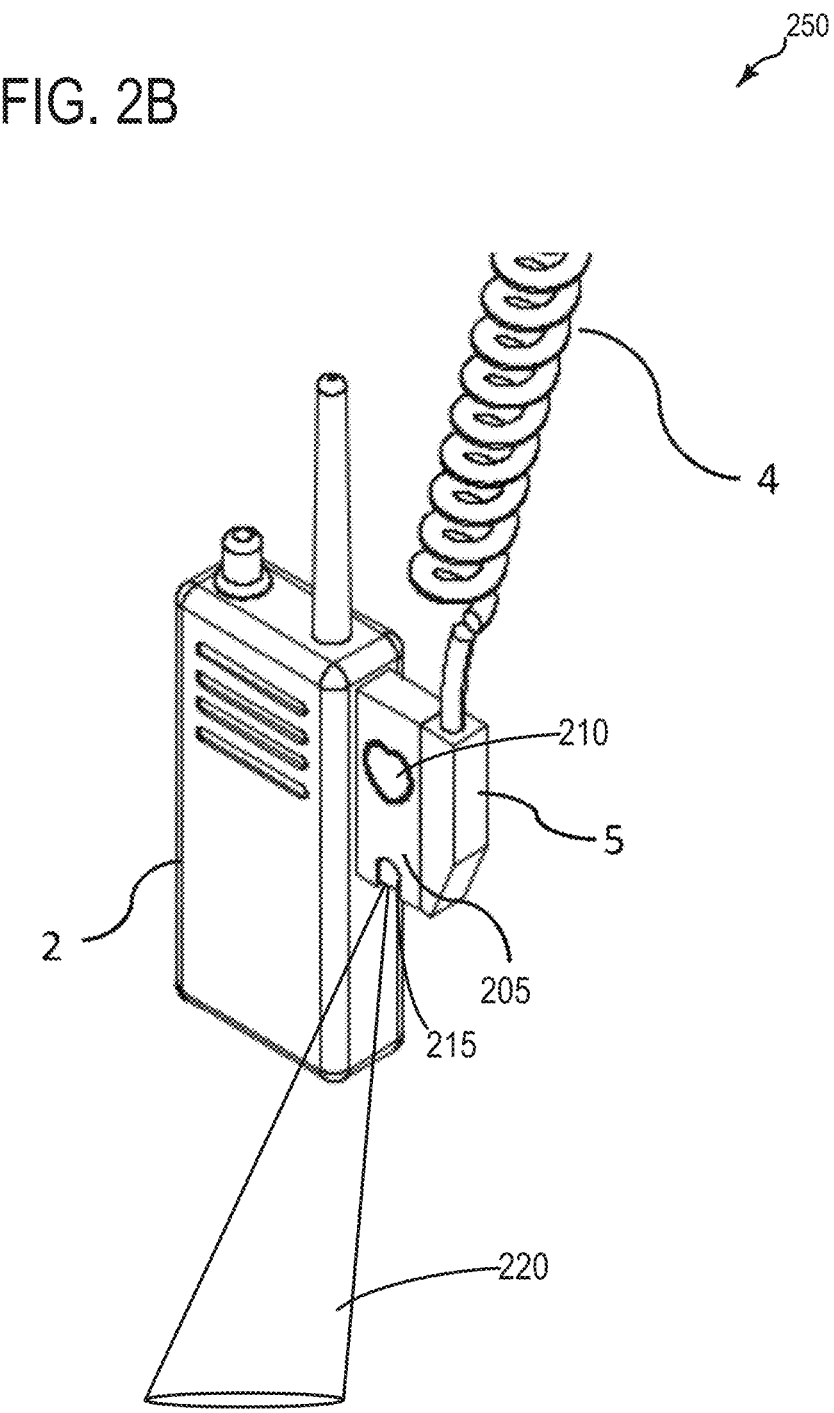
FIG. 2B depicts an example illustration of one embodiment of an alerting device, including an adapter module that couples the RSM to the portable radio, the alerting device capable of providing visual and transmitted alert signals.

Turning now to FIG. 2B, an example illustration 250 depicts another view of adapter 205 (e.g. alerting device 101). At illustration 250, adapter 205 is depicted as being sandwiched between RSM connector 5 coupled to existing retractile cable 4, and portable radio 2. As discussed above, while depicted as being coupled between RSM connector 5 and portable radio 2, it may be understood that in other examples where portable radio 2 couples wirelessly to a RSM (e.g. 3) via a dongle (not shown), then the adapter 205 may be sandwiched between the dongle and the portable radio 2 (in similar fashion as that depicted at FIG. 2B where the adapter 205 is sandwiched between the RSM connector 5 and portable radio 2). Adapter 205 may include a status check actuator 210, the function of which will be discussed in further detail below. It may be understood that status check actuator 210 may comprise a button that can be depressed, a slidable actuator, etc.

Adapter 205 may allow for alerting a wearer of the adapter 205 and nearby fellow firefighters/first responders of a level of stress that the wearer of the adapter is experiencing. As will be discussed in further detail below, the level of stress indicated may be based on one or more physiological parameters, including but not limited to heart rate, body temperature, oxygen saturation, respiration level, activity level, etc. The level of stress may in some examples be based on personalized thresholds. For example, the personalized thresholds may take into account one or more personal factors such as age, gender, family history, pre-existing conditions, presence or absence of hypertension, whether or not the individual smokes or has smoked, cholesterol levels, physical fitness levels, or any other relevant personal physiological parameters which may contribute to stress levels while on duty. The personalized thresholds may in some examples additionally or alternatively be a function of environmental parameters including but not limited to environmental temperature, equipment temperature, detected concentration of gases (e.g. poisonous gases such as carbon monoxide or hydrogen sulfide, explosive mixtures, etc.), other chemical hazards, radiological and biological hazards, temperature and/or flow rate of air supply, etc. As will be discussed in further detail below in reference to FIG. 5A-7B, physiological and/or environmental parameters may be communicated wirelessly to adapter 205 via a wearable sensor (e.g. 102) capable of obtaining physiological and/or environmental data pertinent to the firefighter/first responder wearing the portable radio coupled to the adapter.

It is herein recognized that in some firefighting situations, it may be more appropriate to utilize group thresholds for providing alerts (e.g. visual, audio, etc.), rather than relying on individual thresholds. For example, a group threshold may comprise a threshold applied to a number of firefighters/first responders. Group thresholds may be based on similar physiological and/or environmental parameters as those for which individualized thresholds are based. Thus, as discussed herein, it may be understood that the term "personalized thresholds" may encompass either individualized thresholds, group thresholds, or some combination thereof.

One example of a group threshold may comprise a duration of an engagement. For example, after a group of firefighters/first responders has been actively engaged in a particular engagement for a first predetermined duration, a first threshold may be indicated to be crossed. After said group of firefighters/first responders has been engaged in the particular engagement for a second predetermined duration, a second threshold may be indicated to be crossed. After said group of firefighters/first responders has been engaged in the particular engagement for a third predetermined duration, a third threshold may be indicated to be crossed. In such examples, a color and/or pattern of blinking associated with visual alerts may correspond to an indication of how long the firefighters/first responders have been operating in the first duration, how long in the second duration, how long in the third duration, etc. In other words, the color and/or pattern of blinking may indicate how close said firefighters/first responders are to crossing another threshold.

Another example of a group threshold may comprise threshold heart rate(s). For example, for a group of firefighters/first responders, a first threshold heart rate, a second threshold heart rate, and a third threshold heart rate may be set for the group. Accordingly, when a firefighter/first responder of the group crosses one of the thresholds, an alert (e.g. visual, audible, etc. as discussed herein) may be provided in line with the present disclosure. A color and/or pattern of blinking corresponding to a visual alert, for example, may relate to a duration said firefighter has been operating in a particular stress region or zone (e.g. above the first threshold but below the second threshold, etc.).

While a few examples are provided, it may be understood that other examples are within the scope of the present disclosure. For example group thresholds related to duration of exposure to particular environmental hazards, group thresholds corresponding to durations spent at or above particular temperatures, etc.

The use of individualized thresholds as compared to group thresholds may in some examples be a function of the type of engagement that the firefighters/first responders are engaged in. One example engagement may comprise an urban setting (e.g. house or building) where the engagement is high-stress, and short duration. Another type of engagement may comprise a wildland setting (e.g. forest), where the engagement is of a lower stress level, and longer duration. As one example, individualized thresholds may be preferred under some situations of urban engagements, whereas group thresholds may be preferred under other situations of urban engagements. As another example, individualized thresholds may be preferred under some situations of wildland engagements, whereas group thresholds may be preferred under other situations of wildland engagements.

As one representative example, the way in which duration of current stress level is conveyed by patterning of visual alert signal (e.g. blinking) may differ between urban settings and wildland settings. For example, in a high-intensity urban situation, one blink may correspond to a particular stress level experienced for a duration of one minute. Two blinks may correspond to a particular stress level experienced for a duration of two minutes, and so on. Alternatively, in a longer duration firefighting experience (e.g. wildland setting), one blink may correspond to a duration of 10 minutes at a current stress level, two blinks may correspond to a duration of 20 minutes at a current stress level, etc. In both examples, use of individualized thresholds or group threshold(s) are within the scope of this disclosure.

Adapter 205 may include a light source 215. In one example, light source 215 may comprise a high-brightness red-green-blue (RGB) light emitting diode (LED). In this way, a projecting signal light 220 may be of a color that may be produced by some combination of red, green and/or blue light. Specifically, it is well-known that simultaneously mixing two primary-color light sources, such as red and green, creates a secondary color, such as yellow or orange. In other examples, a bicolor LED (e.g. red and green bicolor LED, with the capability to produce yellow or orange) may be used.

Regarding adapter 205 as an alerting device (e.g. 101), there are two data elements which may be desired to be quickly and unmistakably communicated by means of projecting signal light 220: a current level of stress or risk, and an elapsed time or duration under the current level of stress or risk. A level of stress may be represented by color coding: for example, green may comprise a safe level of stress or risk, yellow or orange may comprise an elevated level of stress or risk, and red may comprise a high level of stress or risk. An elapsed time at a given level of stress or risk may be represented by a pattern of intensity changes within a given color, as described in further detail below with reference to FIG. 3.

Figure 3:
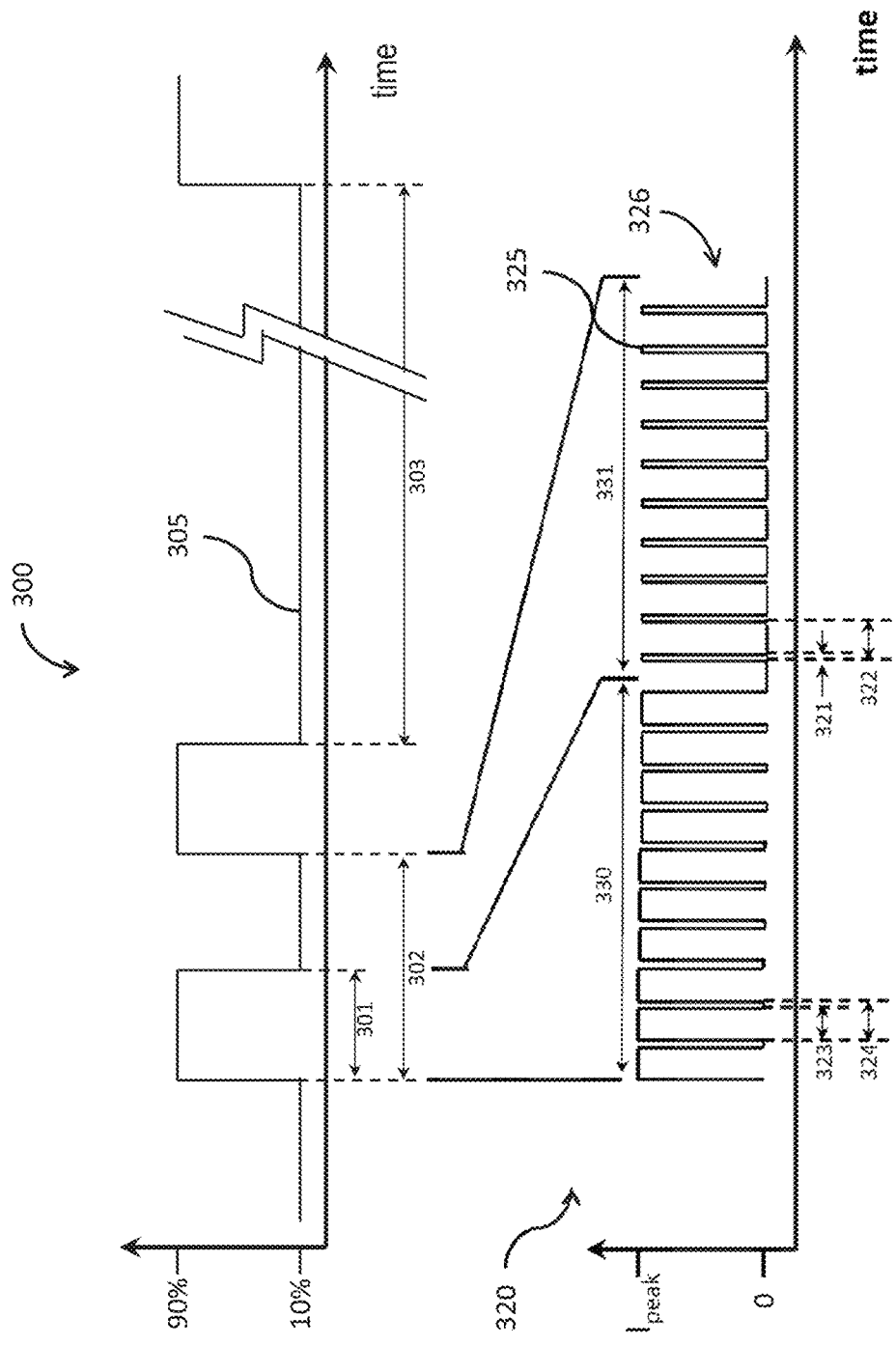
FIG. 3 depicts an example illustration of an example of how to control light sequences of the adapter module depicted at FIGS. 2A-2B.

Accordingly, turning now to FIG. 3, plot 300 depicts a perceived intensity of light emitted from the LED (e.g. light source 215) versus time. For waveform 305, two intensity states are represented: "high" (set as 90% of maximum possible intensity, for example) and "low" (set as 10% of maximum possible intensity, for example). In choosing the intensity states, the "low" state may be sufficient to provide a continuous, detectable background signal, while the "high" state may be perceptible as a "strobe" or "flash" superimposed on a background of the "low" state. To represent a duration of stress, a series of brief flashes of length 301 may be generated at a fixed perceived repetition interval 302 followed by a pause 303 before the cycle repeats. Length 301 is shown for plot 300 as half the duration of perceived repetition interval 302, but length 301 may in other examples be briefer (e.g. less than half) because of phenomena such as persistence-of-vision. As one example, perceived repetition interval 302 may be around 500 milliseconds (2 flashes per second) so that the flashes may be perceived as a distinct series. A practical limit to a number of flashes per cycle may be about 6. Beyond about 6 flashes per cycle, a conscious effort may be required to "count" the flashes. Therefore, representation of stress duration may be scaled to accommodate this practical limit, which may further depend on a given firefighting situation. As examples, in short, intense-stress firefighting engagements (e.g. urban firefighting), with every minute that elapses that a firefighter or first responder is experiencing a particular stress level an additional flash may be provided per cycle. In other words, after experiencing a given stress condition for one minute, one flash per cycle may be provided. After two minutes, two flashes per cycle may be provided, and so on. In other examples, in longer-duration firefighting engagements (e.g. wildland firefighting) or for first responders experiencing relatively lower physical stress (e.g. emergency medical services personnel), a flash per cycle may represent 5 minutes of stress at a particular level, two flashes per cycle may represent 10 minutes of stress at the particular level, and so on. Accordingly, a color progression from green to yellow to red may more rapidly advance in short, intense-stress engagements relative to longer-duration and/or lower-stress engagements. In additional or alternative examples, the representation of stress duration may further depend on personal factors (e.g. age, gender, family history, pre-existing conditions, presence or absence of hypertension, whether or not the individual smokes or has smoked, cholesterol levels, physical fitness levels, etc.).

Continuing with FIG. 3, plot 320 describes a current passed through the LED (e.g. light source 215) (y-axis) versus time (x-axis). Those skilled in the art will recognize waveform 326 as representing a use of pulse-width modulation (PWM) to control LED intensity. PWM represents a more efficient way to control intensity than an analog variation of a LED current. A PWM repetition interval is shown in plot 320 as constant, represented by time intervals 322 and 324, while a duty cycle (e.g. 323, 321) may be varied according to the LED intensity desired. In plot 320, individual PWM pulse trains 325 are shown, during each of a high-perceived brightness period 330 and a low-perceived brightness period 331. As examples, for higher intensities the duty cycle may be 90% (e.g. within high-perceived brightness period 330, interval 323 may be 90% of interval 324), while for lower intensities the duty cycle may be 10% (e.g. within low-perceived brightness period 331, interval 321 may be 10% of interval 322). Note that plot 320 depicts the actual current passed through the LED, whereas plot 300 depicts the perceived intensity of the LED. As such, a time scale of plot 320 has been slowed down relative to a time scale of plot 300 for clarity. In particular, as shown in plot 320, an expansion factor of the time scale is about 10. However, an actual PWM rate may be much higher (e.g. 10 kHz) than that shown, such that said PWM rate may be beyond a visually perceptible range.

Returning to FIG. 2B, the projecting signal light 220 may be projected from adapter 205 in one or more directions. Accordingly, turning to FIG. 4A, an example illustration 400 is depicted, illustrating the potential directionality in which the projecting signal light 220 may be projected from adapter 205. Accordingly, depicted is adapter 205 and portable radio 2. Portable radio 2 includes a face or front 405, and a back 408. Portable radio 2 may further include a right side 410, a left side 415, a top 417, and a bottom 418. Inset 425 depicts a Cartesian coordinate system having x, y and z-axes. Discussed herein, projecting signal light (e.g. 220) may be substantially in a directly downward direction (y-axis) where light is projected from light source 215 in the direction of the bottom 418 of portable radio 2. In this way, light may be projected directly at a floor or ground when portable radio 2 is worn by a firefighter/first responder. An example of such projected signal light is depicted as projecting signal light 430. Additionally or alternatively, projecting signal light may be somewhat inclined toward a forward direction (z-axis), where light is projected from light source 215 outward away from the face 405 of portable radio 2 in order to hit the ground/floor in front of the adapter 205. An example of such projected signal light is depicted as projecting signal light 435. Because portable radio 2 is configured to be worn by a firefighter/first responder in the fashion depicted at FIG. 2A, any light projected backwards (z-axis) outward away from back 408 of portable radio 2 may under most circumstances be projected backward into a body of the firefighter/first responder, which may not be desirable. However, there may be circumstances where it may be desirable to have light project out backward from portable radio 2, such as a case where the portable radio 2 is set down on its face 405, or on its right 410 or left 415 side. Thus, in some examples projecting signal light may additionally or alternatively be inclined somewhat in a backwards direction with respect to the face 405 and back 408 of the portable radio 2.

Figure 4A:
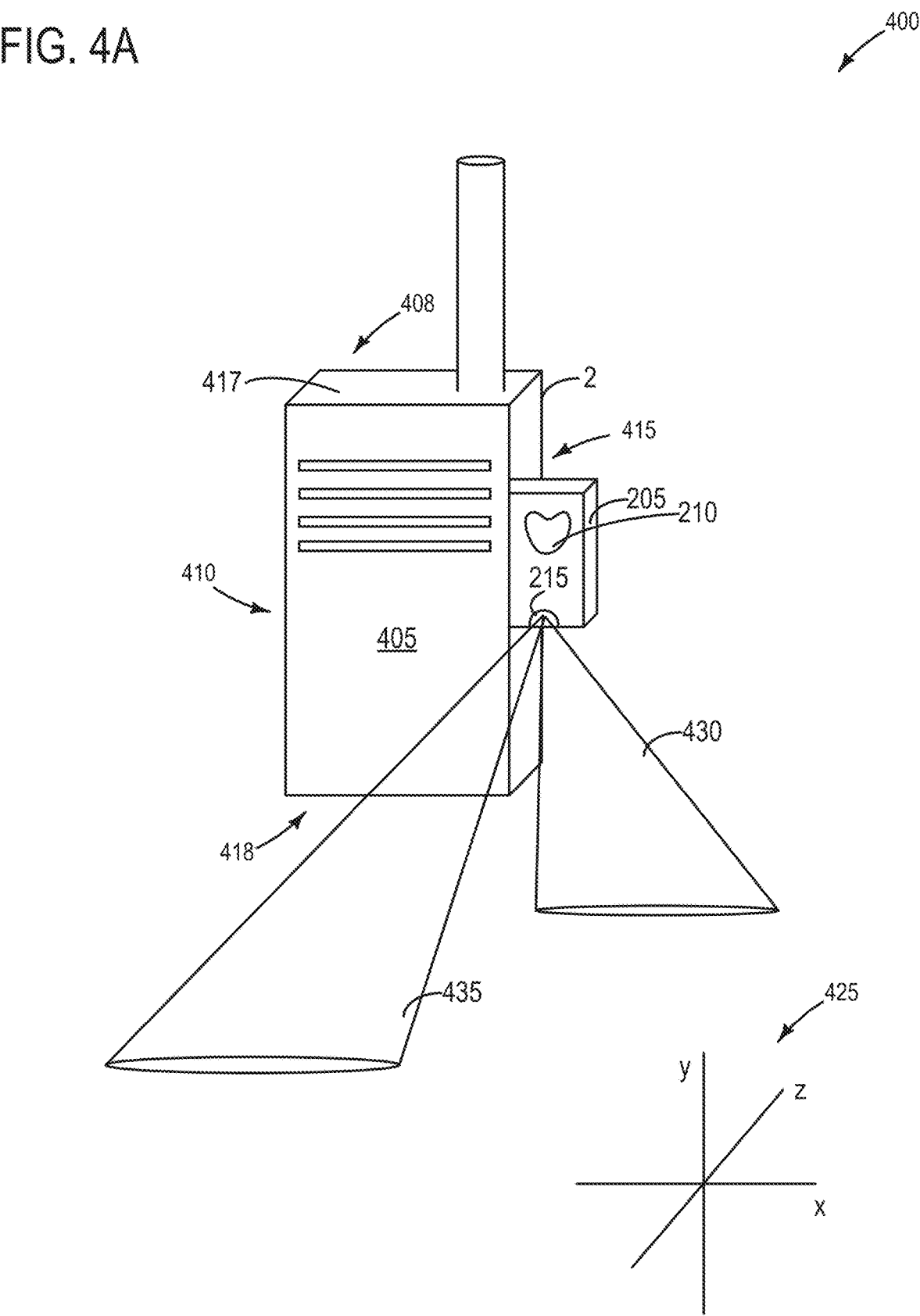
FIG. 4A depicts an example illustration of one or more directions by which a projecting signal light from the adapter module of FIGS. 2A-2B may project.
Figure 4B:
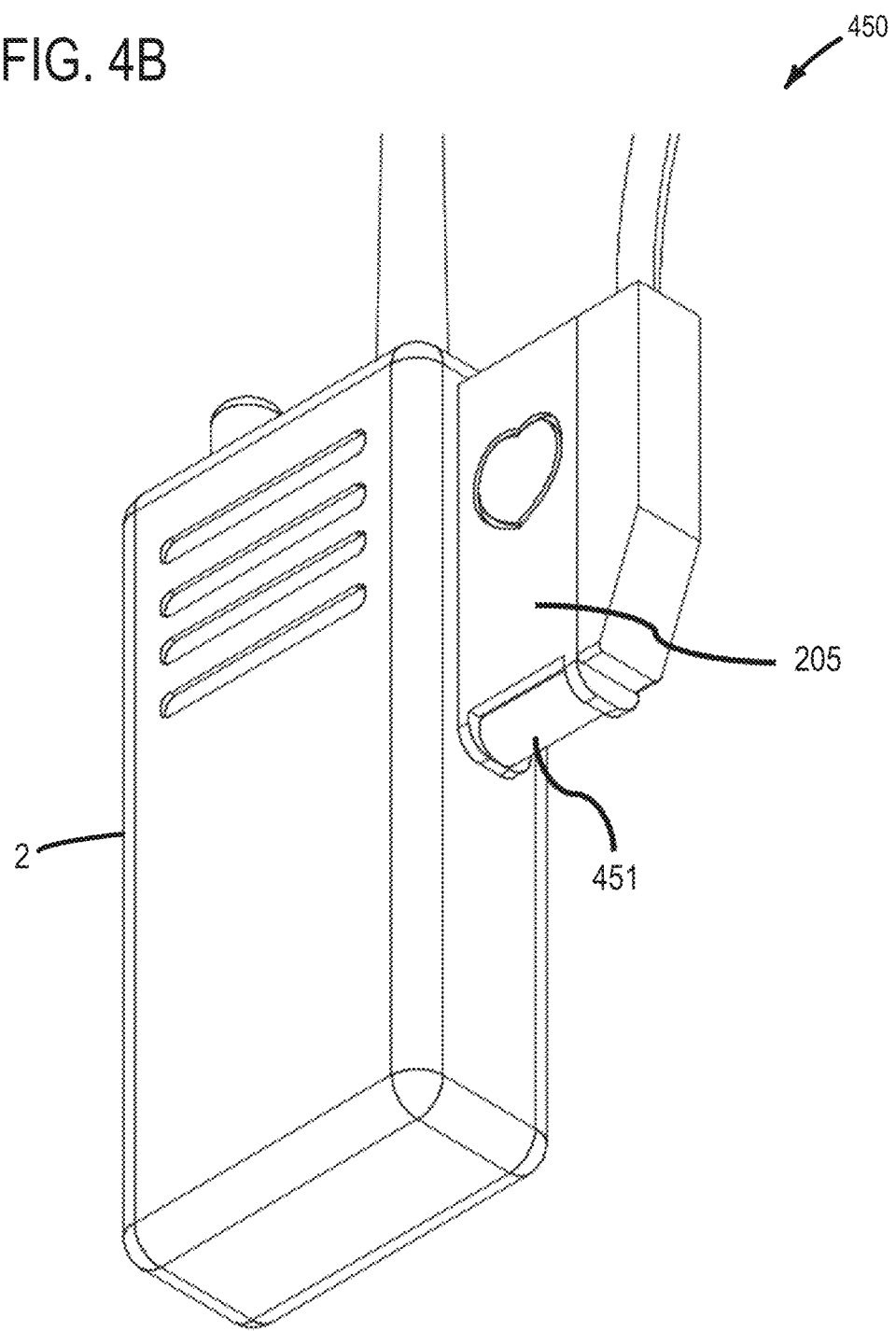
FIG. 4B depicts an alternative view of the adapter module of FIGS. 2A-2B coupled to a portable radio.

Accordingly, turning to FIG. 4B, an alternative view 450 of portable radio 2 and adapter 205 is depicted, illustrating a mechanism to allow a projecting signal light (e.g. 220; not shown at FIG. 4B) to be aimed over a range of angles from forward, downward, or backward. A cylindrical lens and LED assembly 451 may be mounted in the adapter body 205, and may further be pivoted on an axis, such that cylindrical lens and LED assembly 451 may be rotated to face forward, downward, or backward. In additional or alternative examples, cylindrical lens and LED assembly 451 may be retained in position by detents (not shown) so as to not rotate accidentally. Further, by pressing inward on cylindrical lens and LED assembly 451 one or more detents may be overcome so that a different position may be manually set.

As mentioned above, the projecting light (e.g. 220) may be used to convey information at least related to a current level of stress that the wearer of the adapter 205 is experiencing, and may further convey information related to a duration of time the wearer of the adapter has been experiencing a particular stress level. It may thus be desirable for the projecting signal light to be of a high enough brightness and projected in such a way that the wearer of the adapter may be alerted to their current level of stress, as well as in such a way that other nearby firefighters are readily apprised of the current level of stress that a particular individual is experiencing. It may be further understood that it may be desirable for the projecting signal light to be visible to both the wearer of the adapter and to other nearby firefighters under a wide variety of environmental conditions which may be encountered during the course of duty. As one example, in a dark environment that is relatively free from smoke or other airborne particles, the projecting signal light may be visualized as a shape or spot of light on the ground/floor within a predetermined distance or radius of the wearer of the adapter and/or as a light projected along, for example, a leg of the wearer of the adapter. In another example where there is an abundance of light, for example sunlight, artificial light, or light from a nearby fire, the projecting light may be of a brightness where it may still be possible to readily visualize the shape or spot of light on the ground/floor. In still another example where there is an abundance of smoke or other debris filling the area where the wearer of the adapter is performing duties, the projecting signal light may be visualized as a glow resulting from scattering of airborne particles (e.g. smoke particles). In other words, even under circumstances where the projecting signal light does not reach the ground/floor, a glow of a particular color may be readily visualized to both the wearer of the adapter and to other nearby firefighters/first responders.

With regard to FIGS. 4A-4B, it may be understood that there may be a plurality of locations in which a portable radio (e.g. 2) may be carried, such as in a turnout coat pocket, on a leather strap, and/or underneath a user's turnout coat.

In one example, the portable radio may be located on a leather strap, underneath the user's turnout coat, but with the radio extended slightly below the bottom of the coat with the antenna of the portable ratio canted away from the body of the user. In carrying the portable radio in this way, the firefighter/first responder may protect their lifeline by improving signal strength, preventing ejection of the portable radio during active duty, and protecting componentry of the portable radio from potentially melting in high heat environments.

Thus, there may be a particular advantage to the alert system comprising the adapter (e.g. 205) in that the portable radio may be worn underneath the coat of a firefighter/first responder on emergency duty, while the alert signal in the form of projecting signal light may still be visible as the projecting signal light may project from underneath the coat to the floor or ground and/or along a length of a leg of the wearer of the adapter.

Figure 4C:
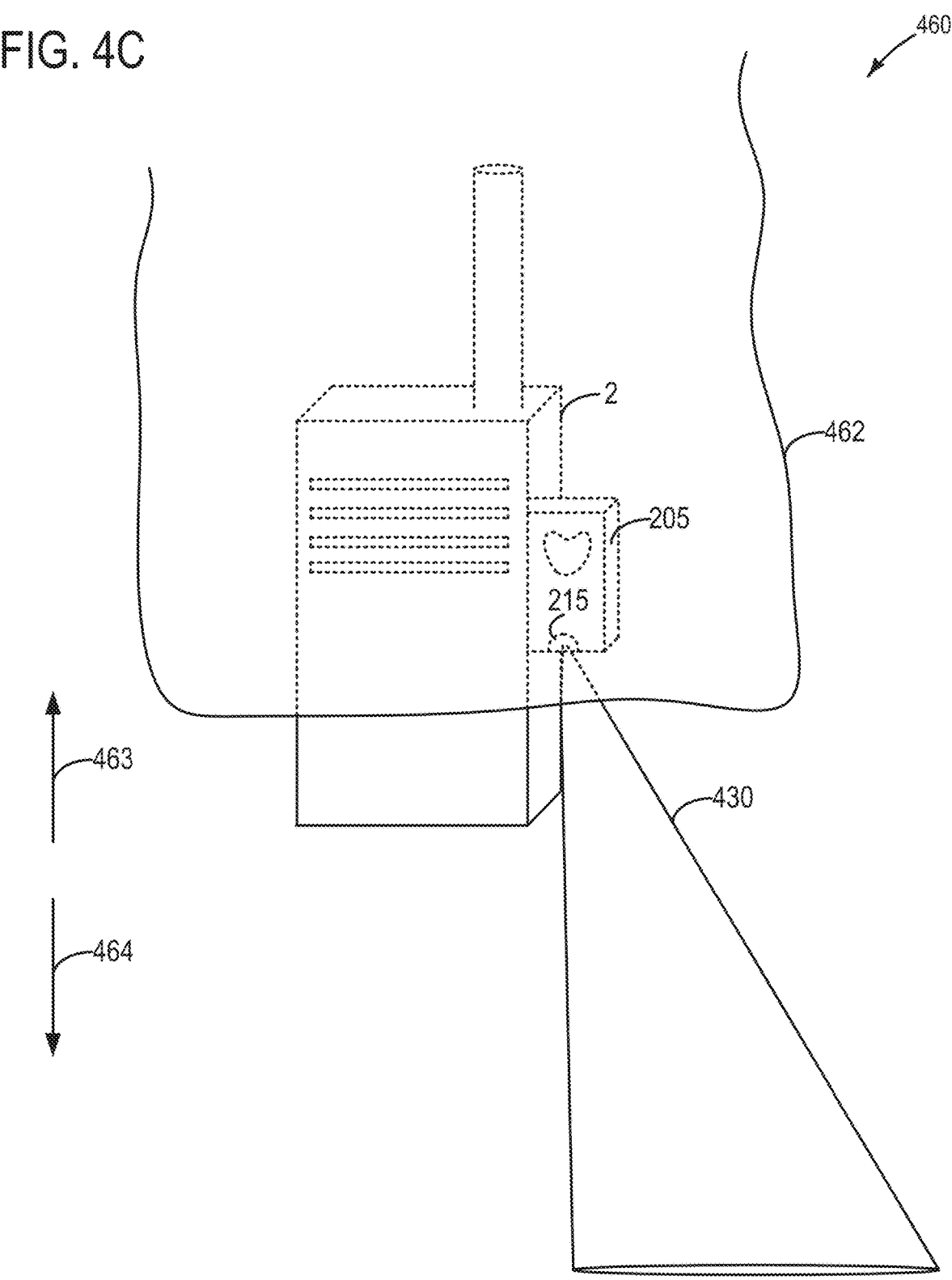
FIG. 4C depicts a first example of how a projecting signal light from the adapter module of FIGS. 2A-2B may emanate from underneath an article of clothing such as a turnout coat.

Turning to FIG. 4C, an example illustration 460 is shown, depicting how the projecting signal light from the adapter (e.g. 205) coupled to the portable radio (e.g. 2) may project out from underneath a turnout coat, for example. Accordingly, FIG. 4C includes similar components as described above at FIG. 4A, and where the same components are discussed, the same numerals are used and are not further defined. Specifically, depicted at FIG. 4C is portable radio 2, electrically coupled to adapter 205 that includes light source 215, capable to project projecting light 430 away from adapter 205 to function as an alert means. Further depicted is a turnout coat 462, where portions of the portable radio 2, adapter 205 and projecting light 430 that are underneath turnout coat 462 are depicted as dashed lines. Alternatively, portions of the portable radio 2, and projecting signal light 430 that are outside of (not underneath) turnout coat 462 are depicted as solid lines. As can be seen at FIG. 4C, when portable radio 2 coupled to adapter 205 is worn underneath turnout coat 462, projecting light 430 may still be projected away from light source 215 without being significantly impeded by the turnout coat 462. Of course, any forward-projecting light may be prevented from escaping the turnout coat 462. However, as long as the downward projecting light 430 is capable of escaping the turnout coat 462, then the alert may still be communicated to the wearer of the portable radio as well as to nearby firefighters/first responders. In this example depicted at FIG. 4C, it may be understood that the firefighter/first responder wearing the portable radio 2 underneath the turnout coat 462 is standing on ground and thus the projecting signal light 430 is projecting towards ground. Accordingly, arrow 463 depicts a direction of the firefighter's head, while arrow 464 depicts a direction of the firefighter's feet which may be understood to be standing on ground (not shown). While the firefighter's legs and feet are not depicted at FIG. 4C, it may be understood that at least part of the projecting signal light 430 may project along the legs and/or feet of the firefighter, which may serve as a way to capture attention of nearby firefighters/first responders. For example, under dangerous stress conditions a leg and/or foot of the firefighter wearing the portable radio and adapter may be illuminated red, which may be readily noticeable to nearby firefighters/first responders.

In additional or alternative examples, as discussed above with regard to FIGS. 3A-3B, the projecting signal light 430 may be operable to execute a series or pattern of blinking to, for example, communicate a severity or type of stress condition. In some examples, the pattern of blinking may be limited to a set, countable number of flashes, wherein a given number of flashes may correspond to a duration a firefighter or first responder has been in a particular stress condition. In such an example, a frequency of blinking may increase with the severity of stress condition. In tandem with the frequency of blinking paradigms, the projecting signal light 430 may illuminate with a color (e.g. green, yellow, red) to further communicate the severity or type of stress condition. For example, a red projecting signal light may indicate a dangerously high stress condition, and where the projecting signal light periodically flashes five times in rapid succession, it may be further indicated that the firefighter or first responder has been in the high stress condition for five minutes.

Figure 4D:
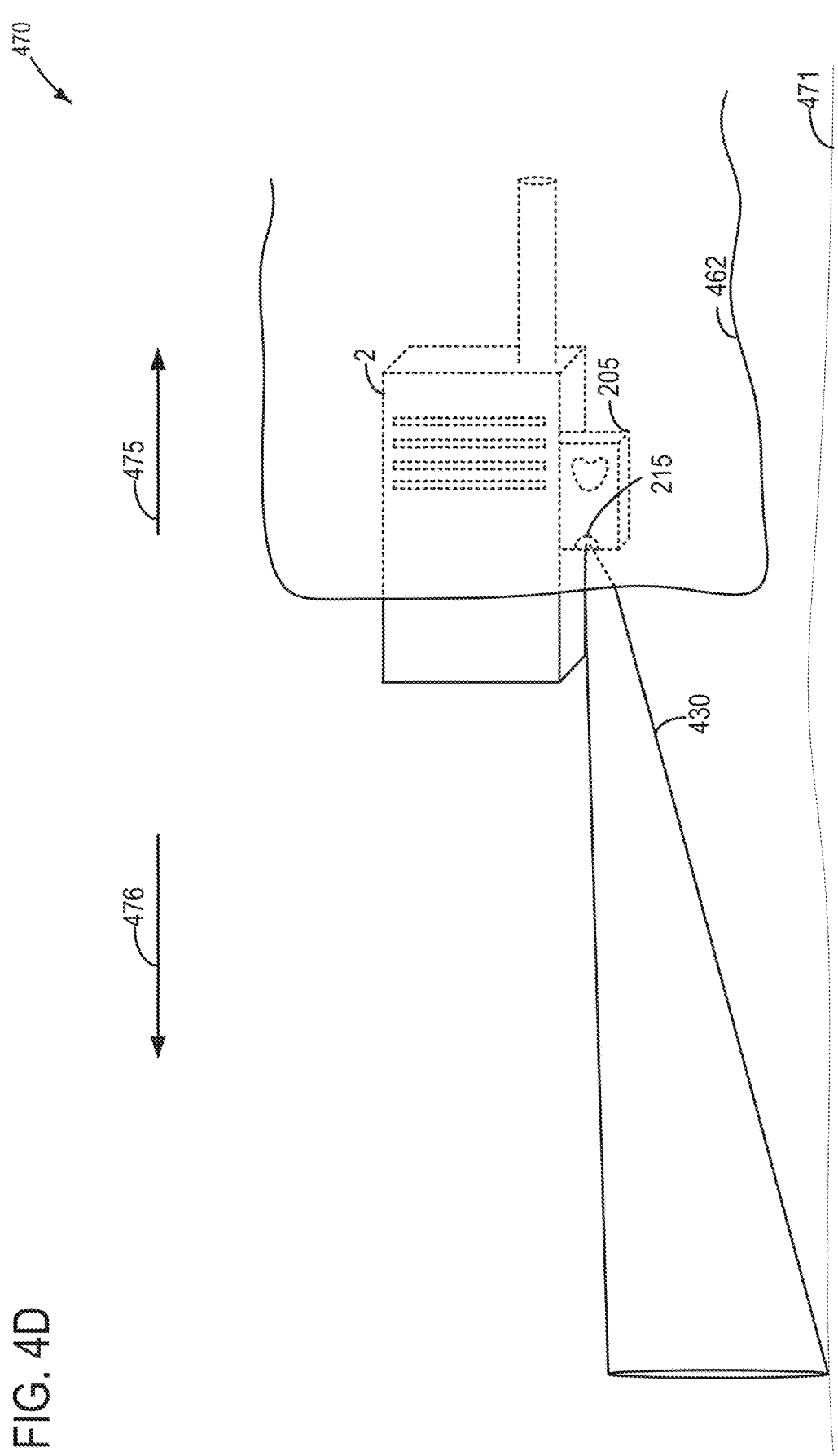
FIG. 4D depicts a second example of how a projecting signal light from the adapter module of FIGS. 2A-2B may emanate from underneath an article of clothing such as a turnout coat.

Turning to FIG. 4D, another related example illustration 470 depicts a situation where a firefighter is crawling along ground. FIG. 4D depicts the same components as depicted at FIG. 4C, and accordingly, components with the same numerals are not further defined. Ground is depicted as 471, and only the turnout coat 462 is depicted as being worn by a firefighter that is crawling along ground 471, while legs, feet, head etc., of the firefighter are not depicted for clarity. As such, arrow 475 points in a direction of the firefighter's head, while arrow 476 points in a direction of the firefighter's feet. As can be seen, even when crawling under circumstances where the portable radio 2 is worn underneath turnout coat 462, projecting signal light 430 escapes from inside turnout coat 462, and is projected at least in part along ground 471. As discussed above at FIG. 4C, it may similarly be understood that at least a portion of projecting signal light may project along a length of leg of the firefighter wearing the portable radio and adapter, which may comprise a visual signal readily seen by other firefighters crawling along, or standing on, ground 471.

Returning to FIG. 2B, adapter 205 may include a status check actuator 210, as mentioned above. Status check actuator 210 may comprise a LED which may be illuminated via a color that is separate from the colors frequently utilized for the projecting signal light 220 (e.g. same as 430). For example, as mentioned above projecting signal light 220 (e.g. same as 430) may be colored green, yellow, or red to indicate varying levels of stress that the individual wearing the adapter may be experiencing, with green exemplifying a safe condition (e.g. no imminent threat of adverse health event), yellow exemplifying a significant stress condition (e.g. stress level to be carefully monitored with at least some action taken to reduce stress where possible), and with red exemplifying a dangerously high stress condition (e.g. high risk of adverse health event if mitigating action is not undertaken immediately). In some examples which will be further elaborated below, projecting signal light 220 may blink in a particular series and/or with a particular frequency to indicate a duration of a particular stress condition. Thus, status check actuator 210 may be illuminated via a color other than green, yellow or red. As one example, status check actuator 210 may be illuminated blue. In some examples, status check actuator 210 may be illuminated during any time in which adapter 205 is in operation.

Status check actuator 210 may comprise a button or slidable actuator that, when depressed or slid, triggers a request for an immediate local voice announcement of the current stress status of the wearer of the adapter 205. The local voice announcement may be broadcast via, as examples, the RSM (e.g. 3) or the portable radio 2. In some examples where the status check actuator 210 is activated, the requested local voice announcement may additionally include information related to physiological data such as heart rate or core temperature of the individual wearing the adapter.

As discussed above, elevated stress levels may persist for some amount of time after actual emergency activity (e.g. active fire suppression) has stopped, making it desirable to continue monitoring of at least physiological (and in some examples environmental) parameters while the firefighter/first responder remains on duty. While in some examples the alerting device (e.g. 101) may continue to be worn by the firefighter/first responder, in other examples it may be desirable to be able to remove said device while still enabling monitoring and alerting to take place. By continuing to wear the wearable sensor (see FIGS. 5A-7B, the wearable sensor may remain in communication with the alerting device (e.g. 101), for example the adapter 205. Thus, in response to an indication of a particular stress condition or environmental condition provided as a function of data retrieved via a wearable sensor (e.g. 102) on the firefighter/first responder, the wearable sensor the wearable sensor may communicate such information to the alerting device (e.g. adapter 205) a local radio announcement may be issued via, for example the RSM (e.g. 3), provided the alerting device is within a predetermined distance of the wearable sensor being worn by the firefighter/first responder 1.

Figure 5A:
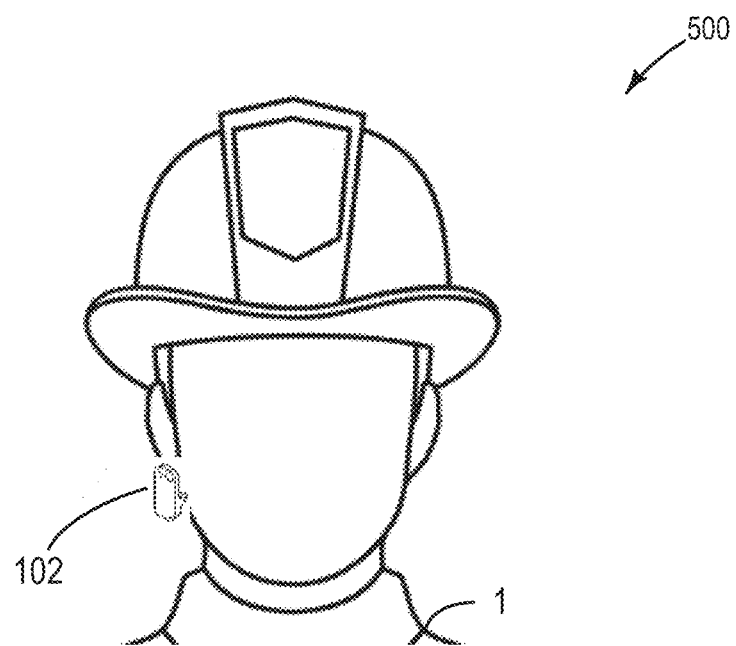
FIG. 5A depicts an example illustration of a wearable sensor.
Figure 5B:
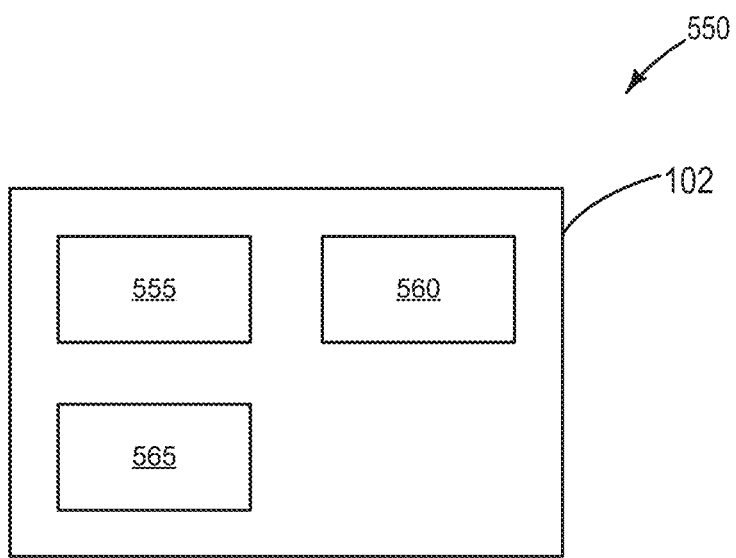
FIG. 5B schematically illustrates example componentry of the wearable sensor of FIG. 5A.

As mentioned above, physiological data and/or environmental data may be communicated to adapter 205 from the wearable sensor. Accordingly, turning to FIG. 5A, an example illustration 500 depicts an example of wearable sensor 102. Specifically, FIG. 5A depicts wearable sensor 102 attached as an ear clip to an earlobe of the firefighter/first responder 1. Wearable sensor 102 may comprise a lightweight but rugged unit intended to be worn at all times while the firefighter/first responder 1 is on duty. Wearable sensor 102 may be equipped to measure one or more of heart rate, body temperature, respiration level, activity level, etc. As examples, wearable sensor 102 may be configured to detect heartbeats using optical plethysmography, electrocardiography, other sensing modalities or a combination of such modalities. Additionally or alternatively, wearable sensor 102 may be equipped to measure one or more environmental parameters such as environmental temperature, concentration of gases within a particular vicinity of the individual wearing wearable sensor 102, concentration of radionuclides within a particular vicinity of the individual wearing wearable sensor 102, etc.

As shown in FIG. 5A wearable sensor 102 is depicted as an ear clip, but in other examples wearable sensor 102 may comprise a wrist band, an upper arm band, a chest strap, shoulder pads, or other location where it is in contact with a skin of the first responder/firefighter 1. However, as discussed above, it may be desirable that wearable sensor 102 not be included within a SCBA or other piece of clothing or equipment that may be removed after emergency duties, such that physiological data and/or environmental data may continually be collected in real time for firefighter/first responder 1 while on duty and not only during emergency duties. In some examples, wearable sensor 102 may be selected via individual firefighters/first responders based on individual comfort level. For example, one firefighter/first responder may prefer to wear wearable sensor 102 as an ear clip, while another firefighter/first responder may prefer to wear wearable sensor as a chest strap. In this way, there may be some leeway in which to achieve full participation from firefighter/first responder departments, such that all firefighters/first responders in some manner wear wearable sensor 102 during the times in which the firefighters/first responders are requested to do so.

Regardless of where wearable sensor 102 may be worn, wearable sensor 102 may contain at least a certain number of elements. Accordingly, turning to FIG. 5B, an example schematic diagram 550 of a wearable sensor 102 is shown. Wearable sensor 102 may include one or more sensors 555 for monitoring physiological and, in some examples, environmental parameters. Wearable sensor 102 may further include a microprocessor 560. Wearable sensor 102 may further include a low-power radio transceiver 565 operable for wireless communications. In some examples, low-power radio transceiver 565 may implement a low energy radio protocol (e.g. Bluetooth), for transmission of physiological and/or environmental data to, for example, the alerting device (e.g. 101, not depicted in FIG. 5B). Furthermore, it may be understood that wearable sensor 102 may be capable of withstanding various types of conditions encountered by firefighters/first responders. For example, wearable sensor 102 may be capable of withstanding high temperatures, be waterproof, be resistant to smoke and other particulates, etc.

Figure 6A:
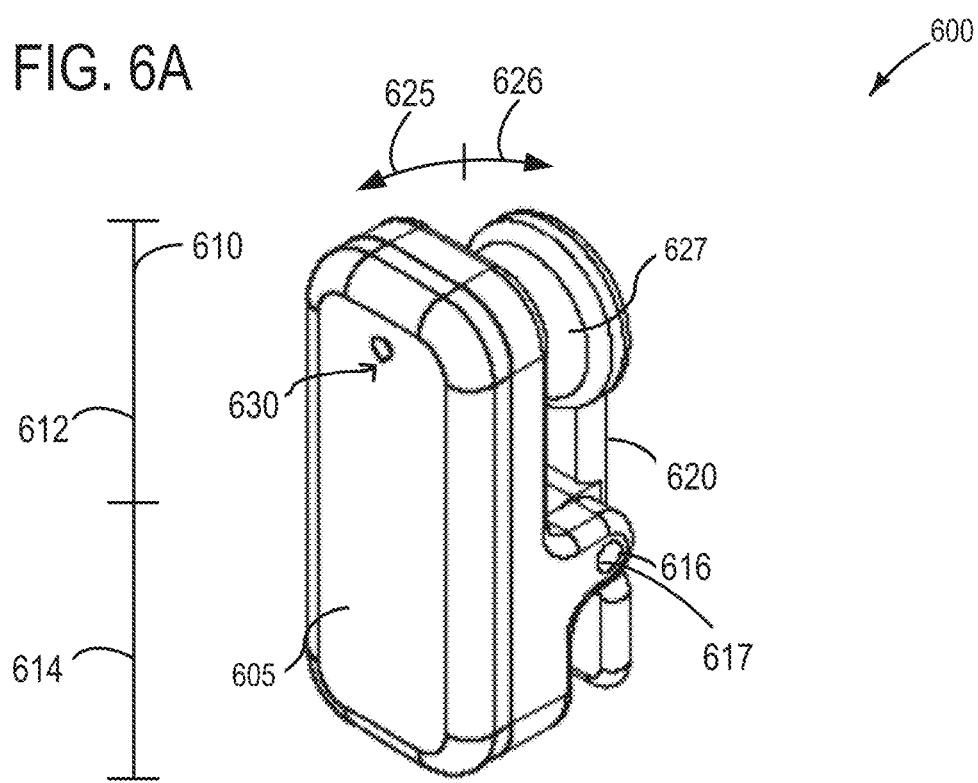
FIGS. 6A-6B depict example embodiments of the wearable sensor of FIG. 5A.
Figure 6B:
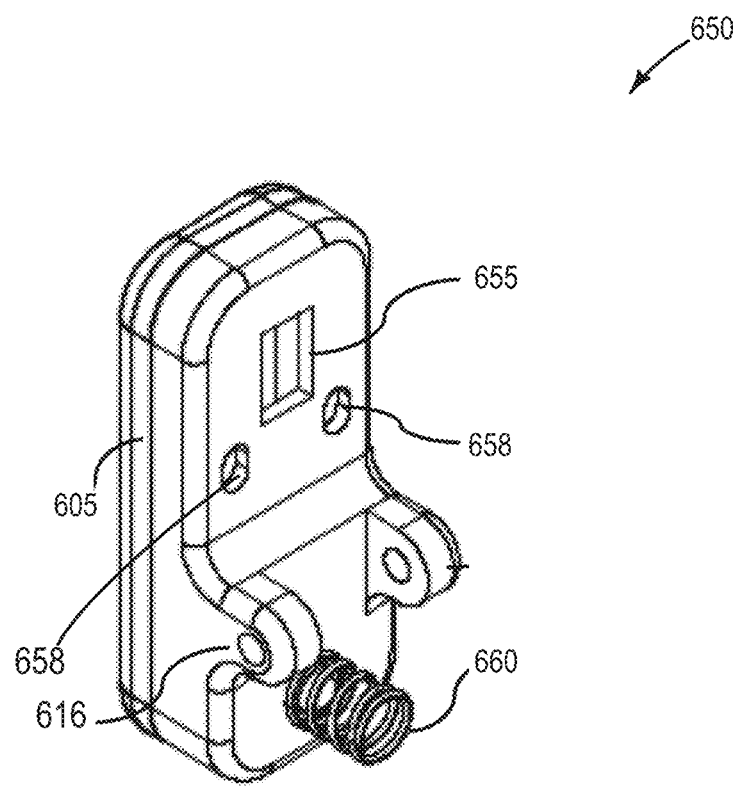

Turning to FIG. 6A, it depicts an example perspective drawing 600 of an example embodiment of a wearable sensor (e.g. 102). The wearable sensor includes a case 605. In an example, case 605 is made of a heat-resistant material including but not limited to silicone rubber and is of a suitable size for clipping onto an earlobe. For example, a length 610 of the wearable sensor may comprise 25-35 mm, where a top half 612 comprises a portion of the wearable sensor that attaches to the earlobe, while a bottom half 614 comprises a portion of the wearable sensor that hangs downward from the earlobe. Two hinge bosses 616 (only one is shown at FIG. 6A but each is shown in FIG. 6B) each include a transverse hole 617 for engagement of a hinge pin (not shown) between them. A hinged clip 620 may be retained via the hinge pin with case 605 such that hinged clip 620 may tilt toward 625 or away 626 from case 605. An upper portion of hinged clip 620 may press against a back of the earlobe via a silicone rubber pad 627, where silicone rubber pad 627 comprises a softer material than cover 605. In some examples, the wearable sensor may include an aperture 630 for an LED indicator.

Turning to FIG. 6B, an alternative view 650 of the wearable sensor (e.g. 102) depicted at FIG. 6A is shown. At FIG. 6B, hinged clip 620 is not shown in order to illustrate other aspects of the wearable sensor. Depicted is a sensor aperture and lens 655. Sensor aperture and lens 655 may be positioned where the earlobe is pressed against via pressure from the hinged clip (e.g. 620). Two recessed contacts 658 are depicted, as means for connecting a charger (not shown at FIG. 6B but shown in FIGS. 8A-8B). A compressible element 660 (e.g. a spring, elastomeric foam, etc.) may provide a pressure on a bottom portion of the hinged clip (e.g. 620) which may thus force the upper portion against the earlobe. In some examples, an adjustable element (not shown) bearing on the compressible element 660 may be included to vary a pressure at which the hinged clip (e.g. 620) attaches to the earlobe, for comfort reasons.

Figure 7A:
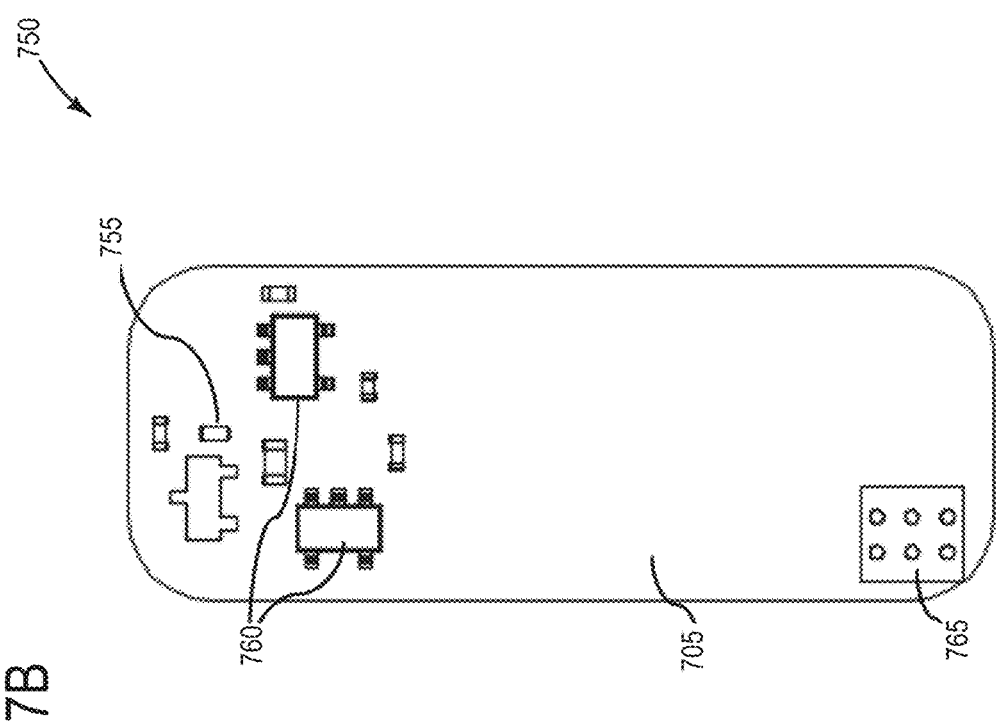
FIGS. 7A-7B depict example embodiments of a printed circuit board for the wearable sensor of FIG. 5A.

Turning to FIG. 7A, an example illustration 700 depicts a first view of an example printed circuit board assembly (PCBA) 705 for implementing the functions of the wearable sensor (e.g. 102). In this first view, PCBA 705 may include a low-power radio transceiver (which, in some examples, may implement a low energy radio protocol; e.g. Bluetooth), antenna, and microprocessor integrated within module 710. PCBA 705 may further include an optical plethysmographic sensor 715 which may include one or more LEDs 718 and a photodetector 720 which may be capable to sense heart rate, oxygen saturation, and optionally other physiological parameters. Two contacts 725 for battery recharging may be included in PCBA 705.

Figure 7B:
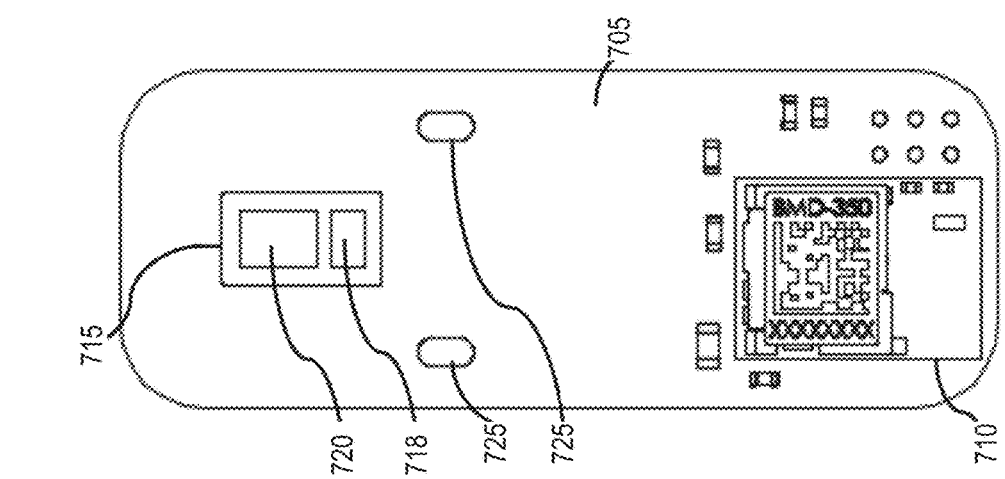

Turning to FIG. 7B, an example illustration 750 depicts a second, opposite view of example PCBA 705. Depicted is an LED indicator 755, battery charging and voltage regulator components 760. PCBA 705 may in some examples include a connector 765 for initial installation of firmware. While not explicitly illustrated, a majority of the second view of PCBA 705 may be reserved for a rechargeable battery.

Figure 8A:
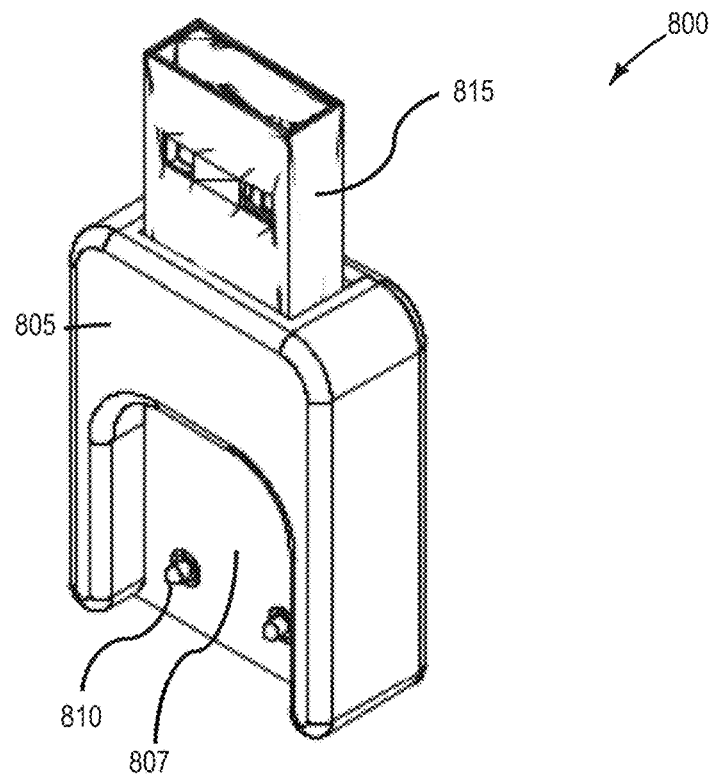
FIGS. 8A-8B depict example illustrations of a charger for the wearable sensor of FIG. 5A.

Turning now to FIG. 8A, an example illustration 800 depicts a perspective drawing of a charger for the wearable sensor depicted at FIGS. 5A-7B. At FIG. 8A, a charger body 805 contains a recess 807 into which the wearable sensor body (e.g. 605) snugly fits. Conductive spring pins 810 may carry charging current to the recessed contacts (e.g. 658) of the wearable sensor (e.g. 102). Low-voltage power (e.g. approximately 5V) may be carried from a male USB plug 815 to spring pins 810, and from there to charging circuitry of the wearable sensor.

Figure 8B:
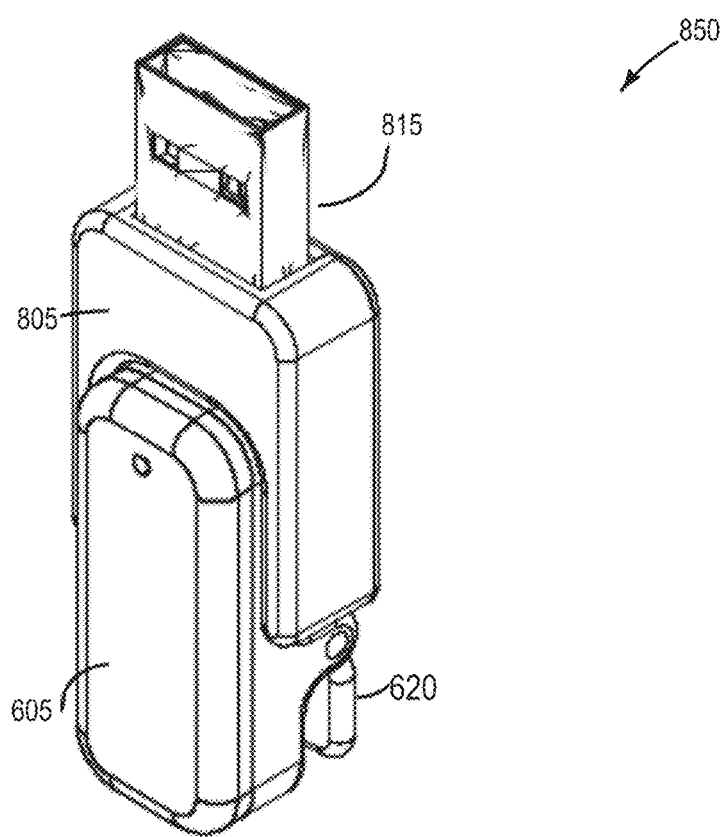

FIG. 8B depicts another example illustration 850, in which wearable sensor body 605 is engaged with charger body 805. Hinge clip 620 maintains pressure on charger body 805 such that conductive spring pins (e.g. 810, not shown in FIG. 8B) are pressed against recessed contacts (e.g. 658, not shown in FIG. 8B) of wearable sensor body 605.

The above description relates to the use of the adapter module (e.g. 205), which may couple to a firefighter/first responder's portable radio (e.g. 2) in the manner as discussed. In another example embodiment, the above-discussed capabilities for an alerting device (e.g. 101) may be incorporated into a microphone/speaker module that may replace an existing RSM (e.g. 3), discussed in detail below. It may be understood that the discussion above relating to personalized thresholds (e.g. individual thresholds or group thresholds) in relation to the adapter module also apply to the discussion below where instead of the alerting device comprising the adapter module, the alerting device comprises a microphone/speaker module, or MS module.

Figure 9A:
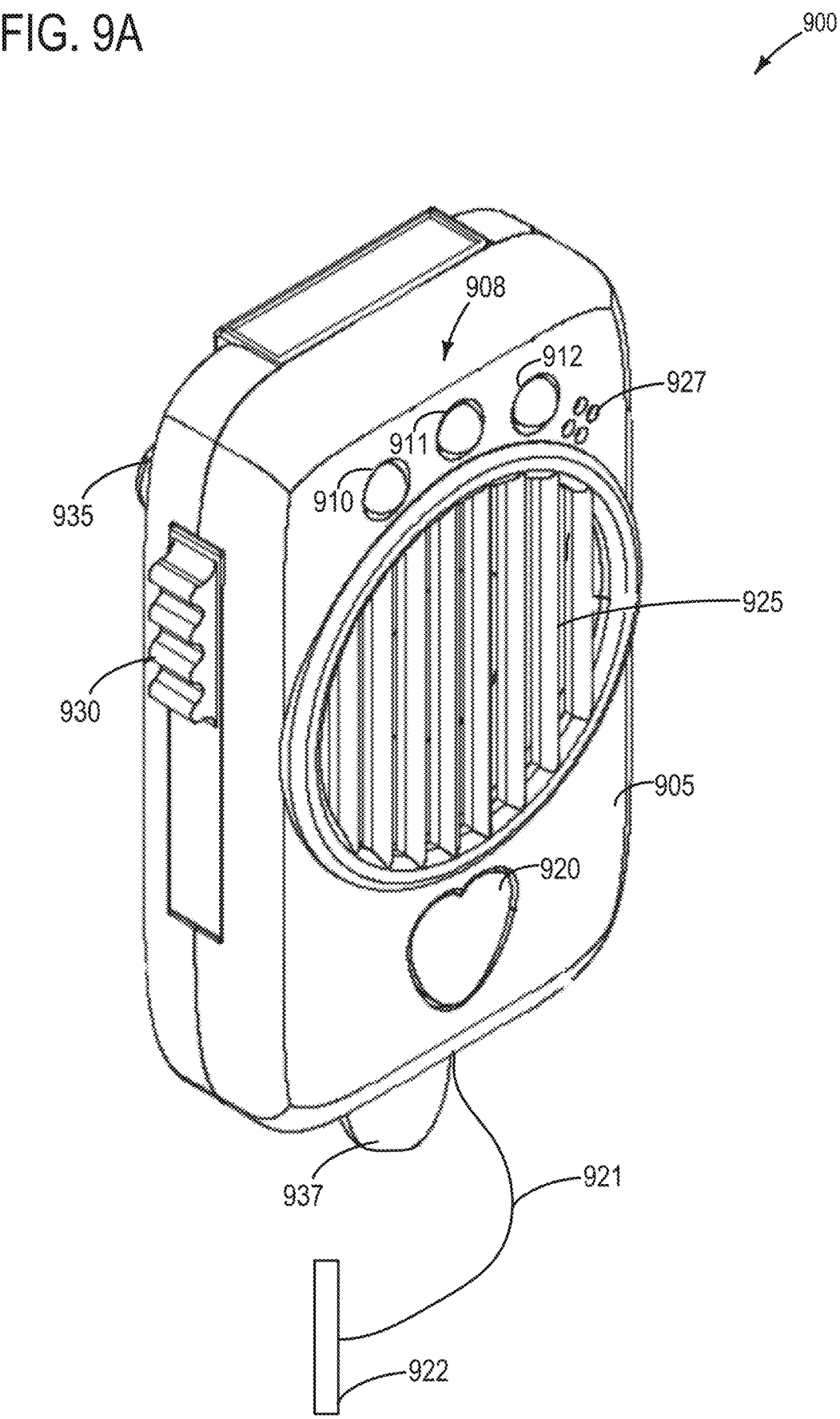
FIG. 9A depicts another example embodiment of the alerting device in an alternate configuration, including a microphone and speaker, such that said device may replace an existing RSM.

Accordingly, turning to FIG. 9A, an example illustration 900 depicts an alerting device (e.g. 101) comprising microphone/speaker, or mic/speak, or MS module 905.

MS module 905 may include a plurality (e.g. three) of signal lights 908. In one example, a first signal light 910 may comprise a green LED, a second signal light 911 may comprise a yellow LED, and a third signal light 912 may comprise a red LED. Similar to the adapter module (e.g. 205) discussed above, MS module 905 may be in wireless communication with a wearable sensor (e.g. 102). The wearable sensor may provide information related to physiological and/or environmental parameters to MS module 905. In turn, MS module 905 may selectively illuminate one or more of the plurality of signal lights 908 in order to provide information as to a level of stress that a particular firefighter/first responder who is wearing MS module 905 may be experiencing. As with the adapter module (e.g. 205) discussed above, and which will be further discussed below, each individual firefighter/first responder may have personalized thresholds set as a function of personal factors such as age, gender, family history, pre-existing conditions, presence or absence of hypertension, whether or not the individual smokes or has smoked, cholesterol levels, physical fitness levels, or any other relevant personal physiological parameters which may contribute to stress levels while on duty. The personalized thresholds may in some examples additionally or alternatively be a function of environmental parameters including but not limited to environmental temperature, equipment temperature, detected concentration of gases (e.g. poisonous gases such as carbon monoxide), detected concentration of radionuclides, temperature and/or flow rate of air supply, etc.

The wearable sensor (e.g. 102) may communicate wirelessly with MS module 905. Such wireless communication may be enabled via preset or pre-established wireless profiles, or in other examples via custom wireless protocols, for example. As an example, the MS module 905 may illuminate the first, green signal light (e.g. 910) to indicate a safe or low stress condition, may illuminate the second, yellow signal light (e.g. 911) to indicate a significant stress situation, and may illuminate the third, red signal light (e.g. 912) to indicate a dangerous stress condition. Furthermore, similar to that discussed for the adapter module (e.g. 205) discussed above, a pattern and/or frequency of blinking of a particular signal light may indicate a duration that the firefighter/first responder wearing MS module 905 has been experiencing a particular stress condition.

MS module 905 may further include a status check actuator 920. Status check actuator 920 may be essentially the same as the status check actuator (e.g. 210) discussed above with regard to the adapter module (e.g. 205), with an exception that status check actuator 920 is located on MS module 905 rather than the adapter. Status check actuator 920 may comprise a LED which may be illuminated in a color different from plurality of signal lights 908. In one example, status check actuator 920 may be illuminated blue. In some examples, status check actuator 920 may be illuminated during any time in which MS module 905 is in operation. Status check actuator 920 may be depressed (or in some examples slid) via the firefighter/first responder wearing the MS module, or via another firefighter/first responder. When activated, status check actuator 920 may request an immediate local voice announcement pertaining to a current stress status of the individual wearing MS module 905. In some examples, the local voice announcement may further comprise information specific to physiological and/or environmental data, for example current heart rate or core temperature of the firefighter/first responder wearing MS module 905.

Accordingly, MS module 905 may include a loudspeaker 925 that may be used to audibly broadcast the local voice announcement. MS module 905 may further comprise a microphone 927, and a push-to-talk actuator 930. MS module 905 may still further include a clip 935 for attachment to clothing and/or equipment, and a cable strain relief 937. It may be understood that all components of MS module 905 may be specified and assembled in a manner meeting applicable standards for resistance to heat, water, shock, and/or other hazards which may occur in environments in which firefighters/first responders operate.

MS module 905 may further include MS module retractile cable 921 and MS module radio interface connector 922, where the MS module radio interface connector communicably couples the MS module to a portable radio (e.g. 2). In alternate examples, MS module 905 may wirelessly couple to MS module radio interface connector in a case where the MS module radio interface connector 922 comprises a dongle.

Thus, as discussed herein, the alerting device (e.g. 101) may in one example comprise the adapter module (e.g. 205), and in other examples may comprise the MS module (e.g. 905). The way in which such modules couple to portable radio 2 are discussed in further detail with regard to FIGS. 9B-9C.

Figure 9B:
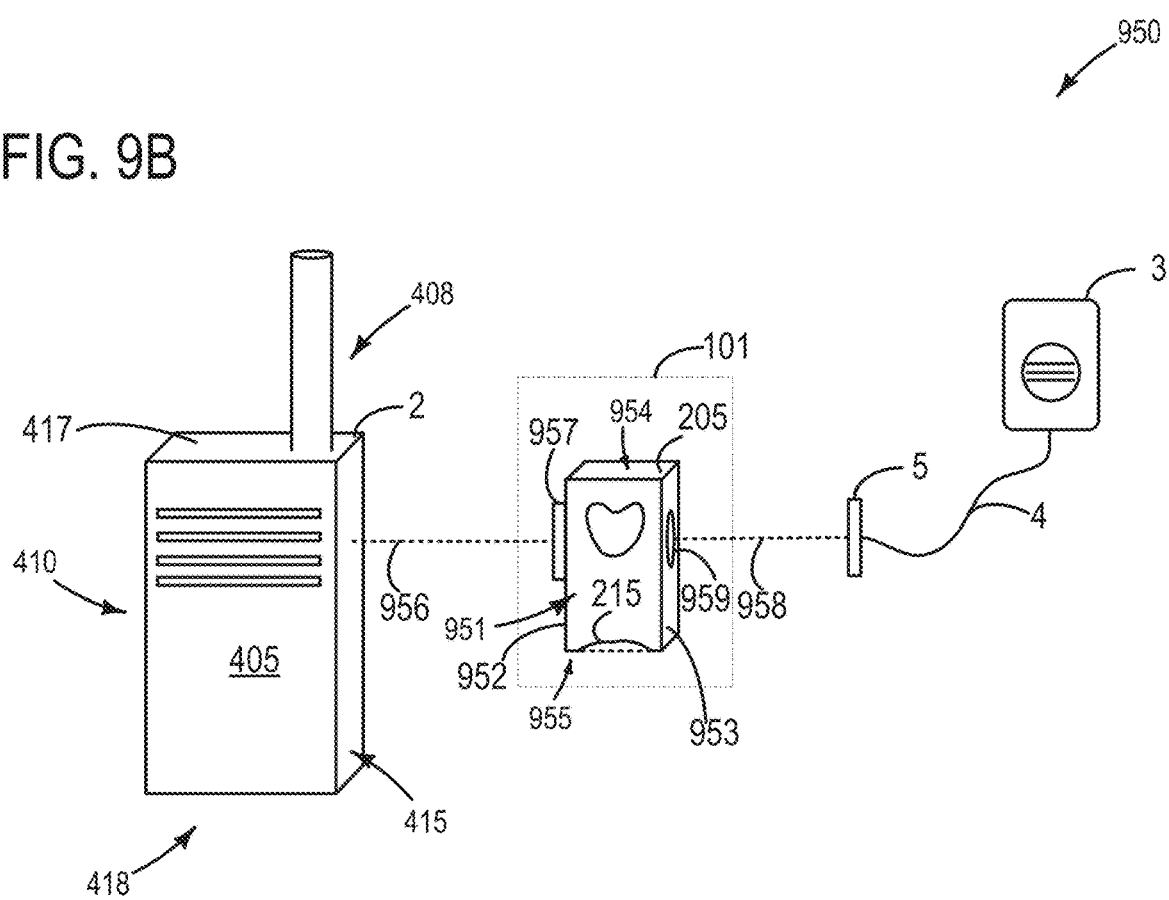
FIGS. 9B-9C depict further illustrations of the alerting devices of the present disclosure.

Turning to FIG. 9B, illustration 950 depicts portable radio 2, alerting device 101 where alerting device 101 comprises adapter module 205, and remote speaker/microphone 3 which includes retractile cable 4 and RSM connector 5. As discussed with regard to FIG. 4A above, portable radio 2 includes a face or front 405, and a back 408. Portable radio 2 may further include a right side 410, a left side 415, a top 417, and a bottom 418.

Adapter module 205 may include a body 951, a first side 952, and a second or opposite side 953. Adapter module may further include a top 954, and bottom 955. It may be understood that signal lights 215 are positioned on the bottom 955 of adapter module 205.

There may be a first interface 956 between the adapter module 205 and portable radio 2. An adapter module radio interface connector 957 may communicably couple adapter module 205 to portable radio 2. There may be a second interface 958 between adapter module 205 and RSM connector 5. An adapter module remote speaker/microphone connector 959 (also referred to as adapter module RSM connector) may be included on adapter 205 for communicably coupling remote speaker/microphone 3 to adapter module 205. It may be understood that adapter module radio interface connector 957 is on an opposite side as adapter remote speaker/microphone connector 959. In this way, as depicted at FIG. 9B, alerting device 101 in the form of adapter module 205 may be communicably coupled to both portable radio 2 and remote speaker module 3. While not explicitly illustrated, it may be understood that in some examples remote speaker module 3 may wirelessly couple to adapter module 205 under cases where remote speaker/microphone connector comprises a dongle.

Figure 9C:
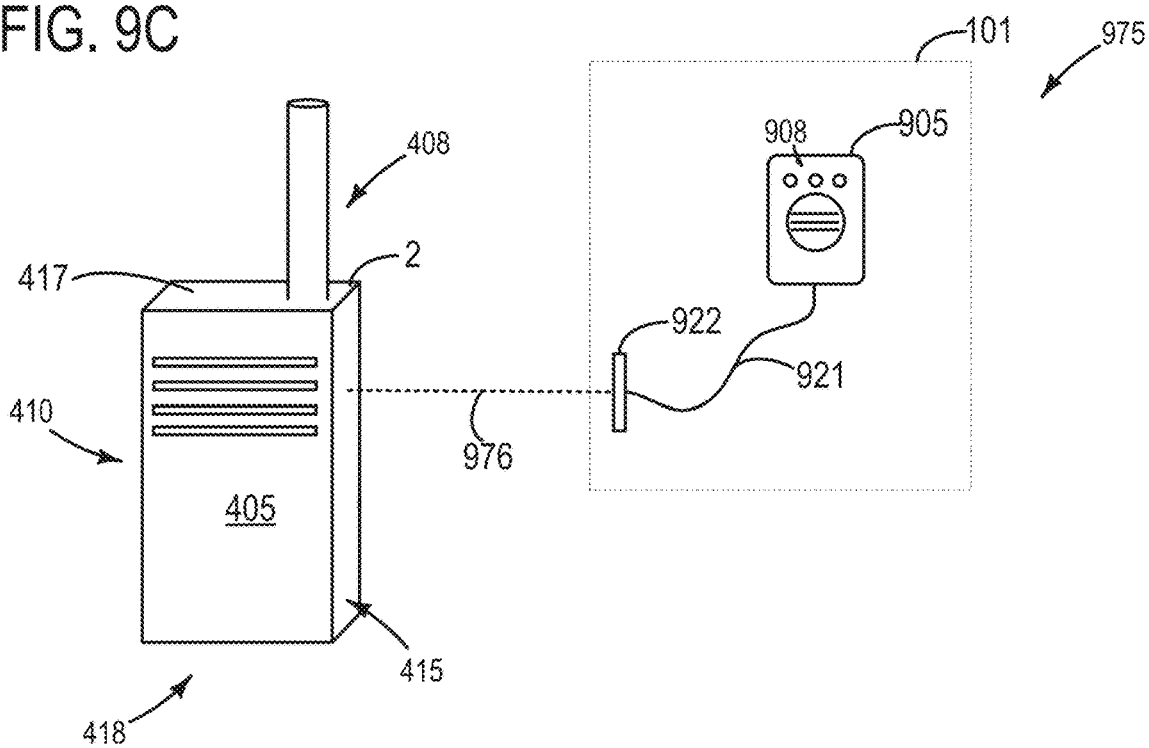

Turning now to FIG. 9C, example illustration 975 depicts portable radio 2, as discussed above with regard to FIG. 9B. Further depicted is alerting device 101, where alerting device 101 comprises MS module 905. As discussed with regard to FIG. 9A, MS module 905 includes MS module retractile cable 921 and MS module radio interface connector 922. There is a third interface 976 between portable radio 2 and MS module radio interface connector 922. It may be understood that MS module radio interface connector 922 communicably couples MS module 905 to portable radio 2. While not explicitly illustrated, it may be understood that in some examples MS module may be communicably coupled to MS module radio interface connector 922 wirelessly, where MS module radio interface connector 922 comprises a dongle.

While discussed above the radio interface connector is referred to as adapter module radio interface connector and MS module radio interface connector, it may be understood that such connectors may simply be referred to as a radio interface connector for alerting device (e.g. 101), which may encompass either the adapter module or the MS module.

Figure 10A:
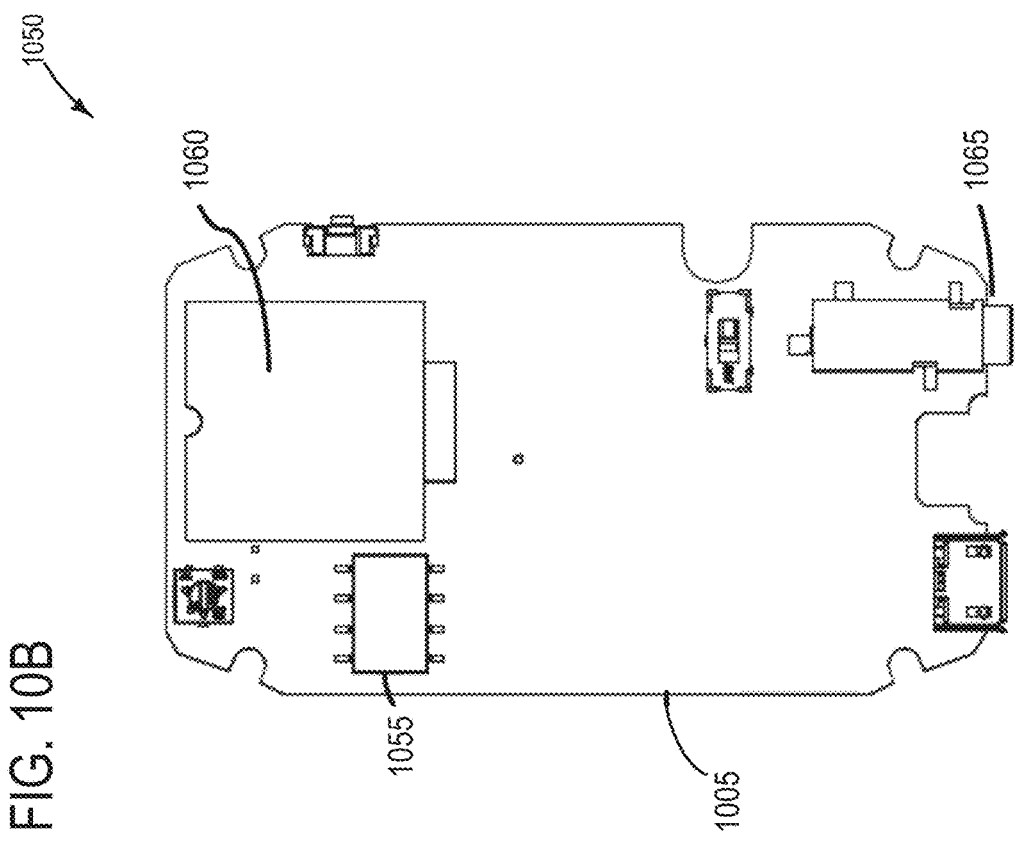
FIGS. 10A-10B depict example illustrations of a printed circuit board corresponding to the embodiment of FIG. 9A.
Figure 10B:
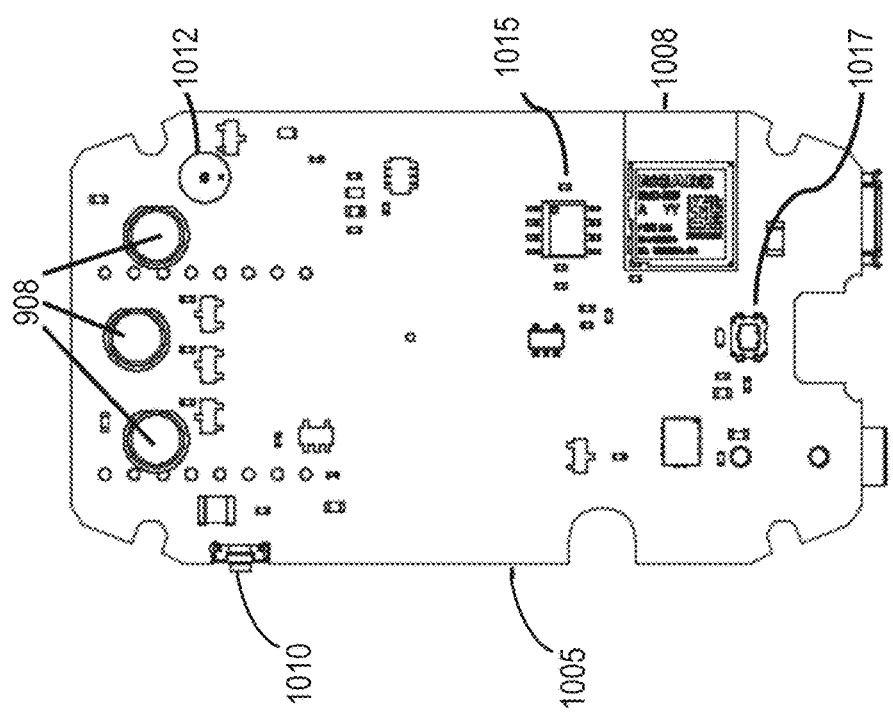

FIGS. 10A-10B illustrate a printed circuit board corresponding to a MS module (e.g. 905). It may be understood that one or more components of said printed circuit board may be the same as, or similar to, analogous components in an adapter module (e.g. 205). Turning now to FIG. 10A, an example illustration 1000 of a first side of a printed circuit board 1005 corresponding to the MS module is shown. In this example, a low-power radio transceiver (which, in some examples, may implement a low energy radio protocol; e.g. Bluetooth), antenna, and microprocessor are combined in module 1008. Also depicted is a side-actuated push-to-talk actuator 1010, the plurality of LED signal lights 908, a microphone element 1012, a flash memory chip 1015, and electronics/LED 1017 corresponding to a status check actuator (e.g. 920). It may be understood that, in some examples, flash memory chip 1015, one or more components of module 1008, such as the microprocessor, and various input/output ports may be included in a single processor, or controller, or microcontroller.

Turning to FIG. 10B, an example illustration 1050 of a second side of the printed circuit board 1005 is shown. Depicted is an audio routing switch 1055, for example a sealed electromechanical relay, an audio file decoder and amplifier module 1060, and an external microphone/earphone jack 1065.

Figure 11:
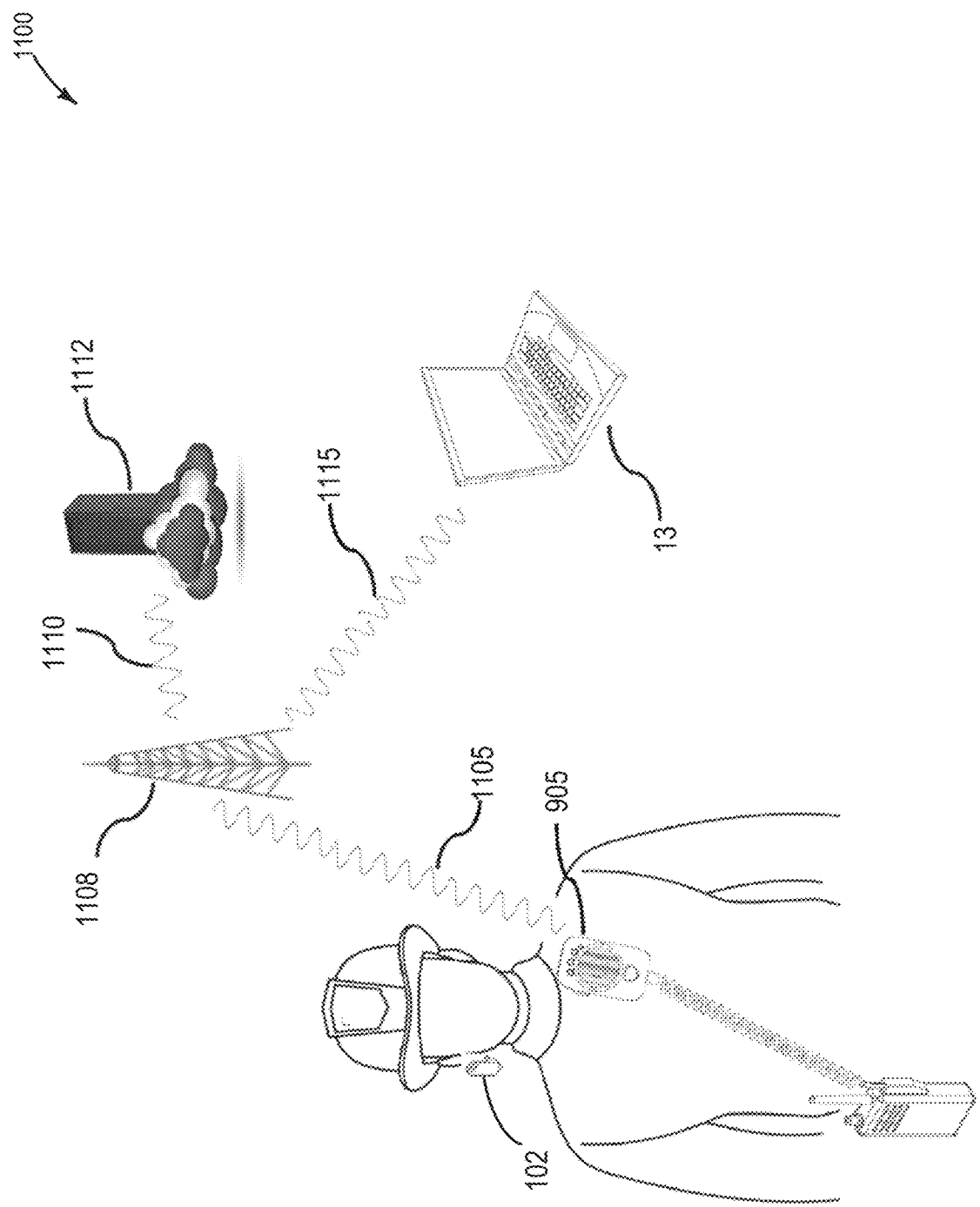
FIG. 11 depicts an example embodiment where a transceiver capable of communicating with a cloud-based server is included in the alerting device.

Whether the firefighter/first responder is equipped with an adapter (e.g. 205) or MS module (e.g. 905), in some examples there may be a transceiver capable of communicating with a cloud-based serve (e.g. cellular transceiver) housed within the adapter and/or MS module. Turning to FIG. 11, an example illustration 1100 of an alerting system (e.g. 100) is shown, depicting a situation where said transceiver is housed within MS module 905. In this way, data pertaining to physiological and/or environmental factors as monitored by wearable sensor 102 may be transmitted via a first radio signal 1105 (e.g. cellular radio signal) to a cell tower 1108. From the cell tower 1108, data may be transmitted via existing wired or wireless networks 1110 to a cloud-based server 1112 (wherein cloud-based server 1112 may be remote server 12 as discussed in reference to FIG. 1). Accordingly, firefighter/first responder data and/or alerts are thus made available via a second radio signal 1115 (e.g. second cellular radio signal) to a mobile data terminal 1120 (wherein mobile data terminal 1120 may be computing device 13 as discussed in reference to FIG. 1). The mobile data terminal 1120 may be located in an incident commander's vehicle, or on person of the incident commander, etc. In some examples, second radio signal 1115 may issue text message alerts to the incident commander. It may be understood that the wireless network depicted at FIG. 11 may comprise network 11 as discussed above at FIG. 1.

Figure 12A:
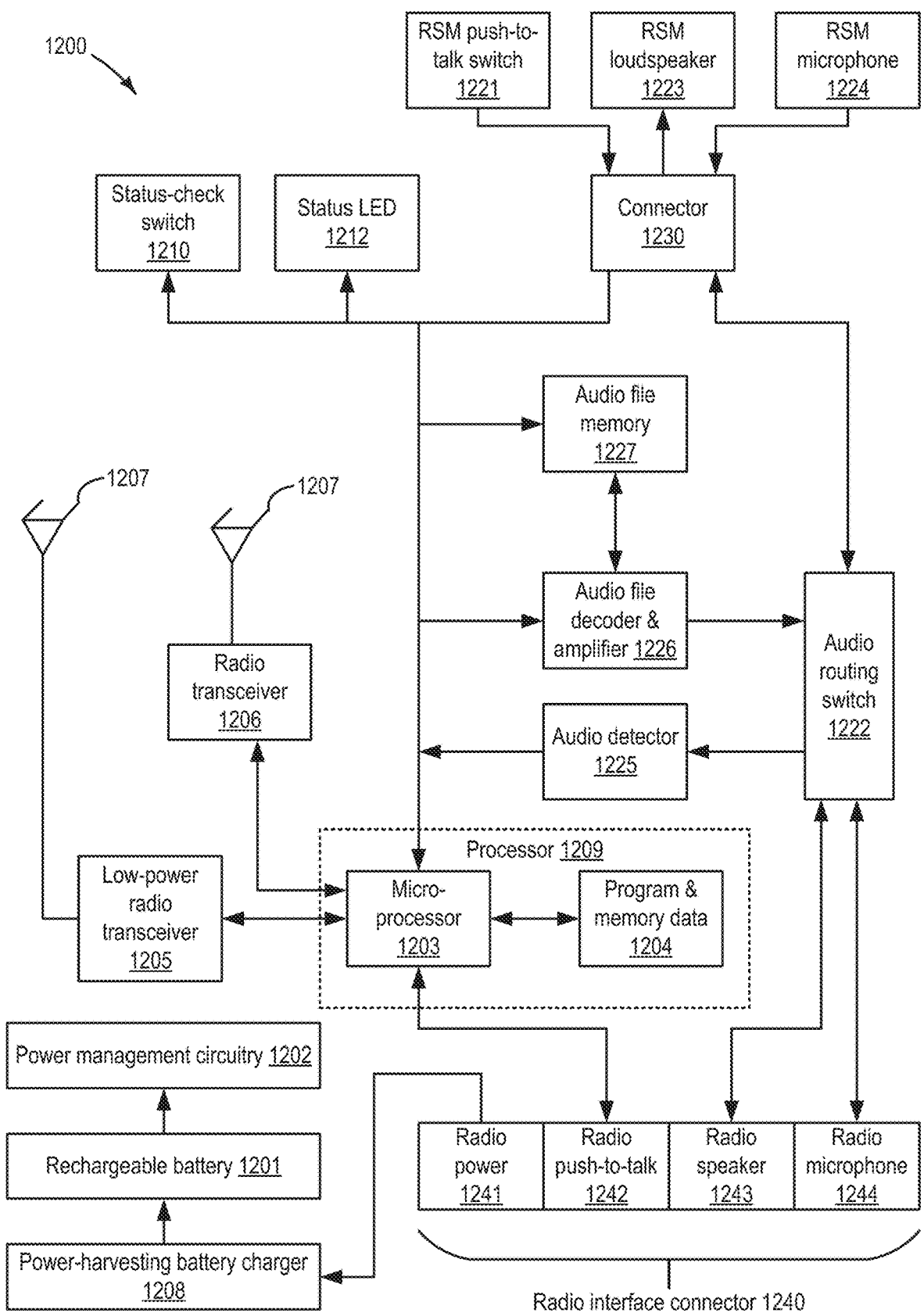
FIG. 12A depicts a block diagram of example electronic circuitry of the embodiment of FIGS. 2A-2B.
Figure 12B:
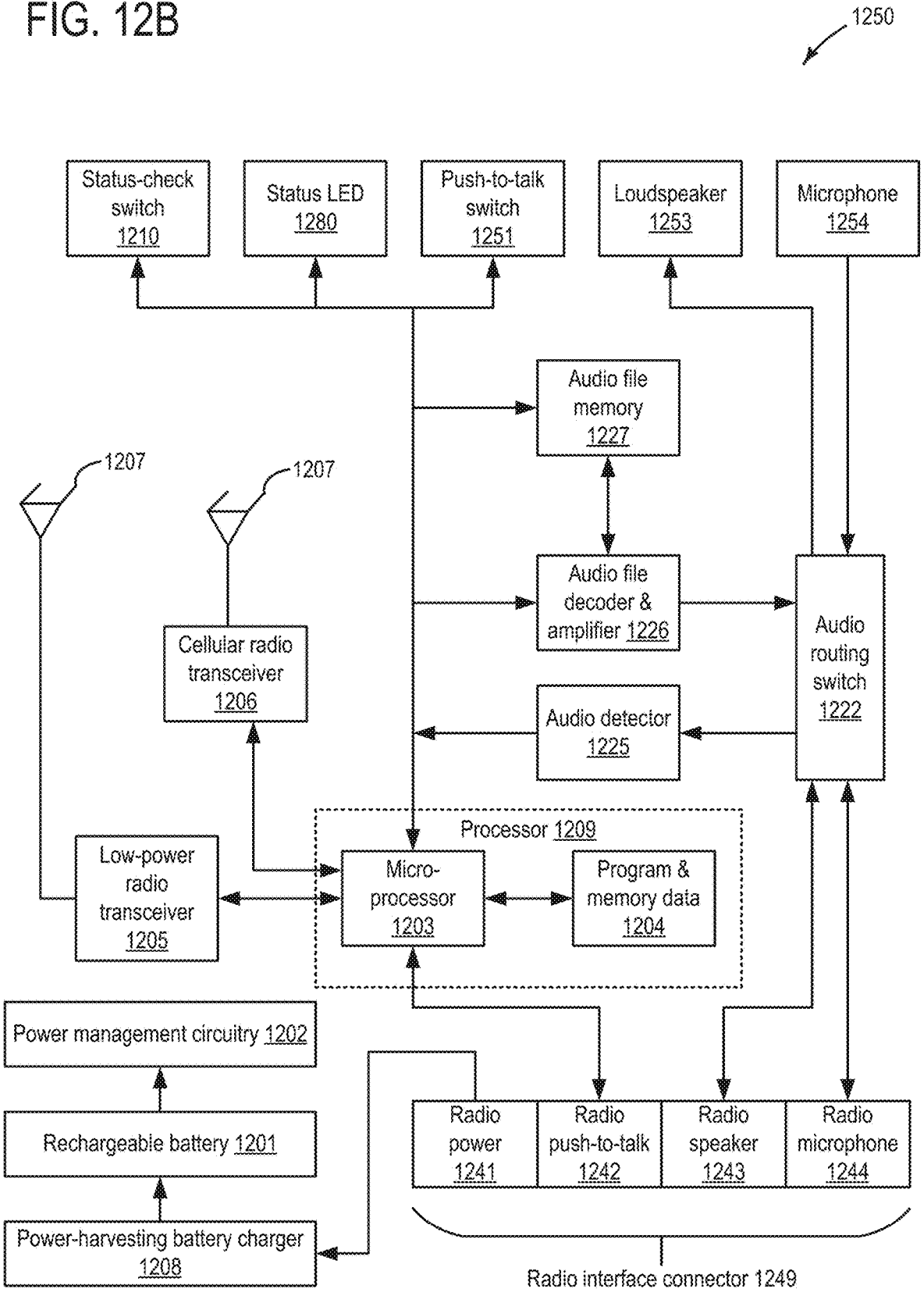
FIG. 12B depicts a block diagram of example electronic circuitry of the embodiment of FIG. 9A.

At FIGS. 12A-12B, example block diagrams are depicted of electronic circuitry within an alerting device (e.g. 101), specifically of electronic circuitry within an adapter (e.g. 205) or MS module (e.g. 905), as well as interfaces with other components of the alerting system (e.g. 100), such as the portable radio (e.g. 2) and the RSM (e.g. 3). Turning now to FIG. 12A, it depicts an example block diagram 1200 of electronic circuitry within the adapter module, as well as interfaces with the portable radio and RSM. A rechargeable battery 1201 provides power to all circuitry depicted at FIG. 12. Regulation of said power may be provided at a power management circuitry 1202. Further, rechargeable battery 1201 may be recharged by a power-harvesting battery charger 1208, wherein power-harvesting battery charger 1208 harvests radio power 1241 from a portable radio (e.g. 2) via an adapter module radio interface connector 1240 (e.g. same as 957). Alerting device (e.g. 101) power consumption may be characterized by shorter bursts of high-power use (e.g., spoken announcements, LED pulses, etc.) interspersed with much longer periods of very low power consumption. As a result, a net average power consumption by the alerting device may be low enough such that rechargeable battery 1201 may be trickle-charged using modest current amounts harvested via power-harvesting battery charger 1208. In examples wherein adapter module radio interface connector 1240 includes a connection to a portable radio battery, radio power 1241 may be harvested from said portable radio battery. Additionally or alternatively, a microphone bias potential may be harvested when a radio microphone 1244 from the portable radio is not in use.

A microprocessor 1203 may be in communication with program and memory data 1204, as well as a low-power radio transceiver 1205. In some examples, low-power radio transceiver 1205 may implement a low energy radio protocol (e.g. Bluetooth). In one example, microprocessor 1203, program and memory data 1204, and low-power radio transceiver 1205 may comprise a single integrated circuit. It may be understood that, in some examples, microprocessor 1203, program and memory data 1204, and various input/output ports may be included in a single processor, or controller, or microcontroller, 1209. In one example, another radio transceiver 1206 (e.g. cellular radio transceiver, or in other words, transceiver of a greater power than transceiver 1205) may be included, also in communication with microprocessor 1203. Transceivers 1205 and 1206 may be equipped with separate or combined antennas 1207. In some examples transceivers 1205 and 1206 may be the same transceiver, in other examples said transceivers may be different.

Figure 13A:
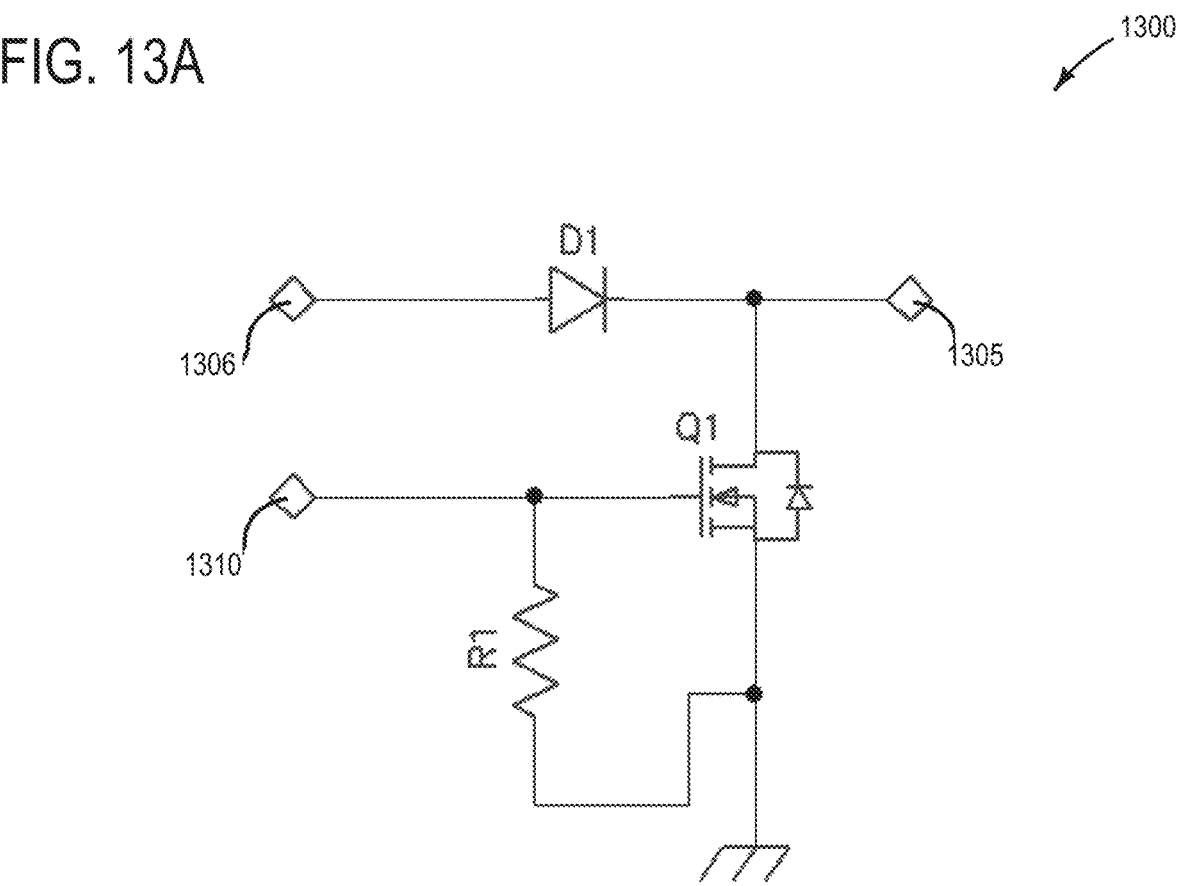
FIG. 13A depicts an example illustration of circuitry connecting the embodiment of FIG. 9 to a push-to-talk line of a portable radio.

A status-check switch, or actuator, 1210 may be sensed via an input pin of microprocessor 1203, and an illuminating LED within switch 1210 may be controlled by an output pin of microprocessor 1203. A radio push-to-talk line 1242 from the portable radio (e.g. 2) may be connected via adapter module radio interface connector 1240, and may also be connected to input/output pins on microprocessor 1203 via circuitry (as shown in FIG. 13A) that prevents situations where an exhausted battery in the RSM (e.g. 3) pulls a push-to-talk line (e.g. 1221) to ground and falsely initiates a transmission. Further, status LEDs 1212 may comprise a high-brightness RGB LED, a bicolor LED, etc., and may also be controlled via output pins of microprocessor 1203, in some examples via high-current driver circuits. Brightness and sequencing of illumination of status LEDs 1212 may be controlled via PWM, for example (as shown in FIG. 3).

A RSM push-to-talk switch, or actuator, 1221, waterproof RSM loudspeaker 1223, and waterproof RSM microphone 1224 may be included on the RSM (e.g. 3), interfaced to the adaptor module (e.g. 205) via a adapter module RSM connector 1230 (e.g. same as 959). Specifically, RSM push-to-talk switch 1221 and each of RSM loudspeaker 1223 and RSM microphone 1224 may connect to microprocessor 1203 and audio routing switch 1222 via adapter module RSM connector 1230.

Figure 13B:
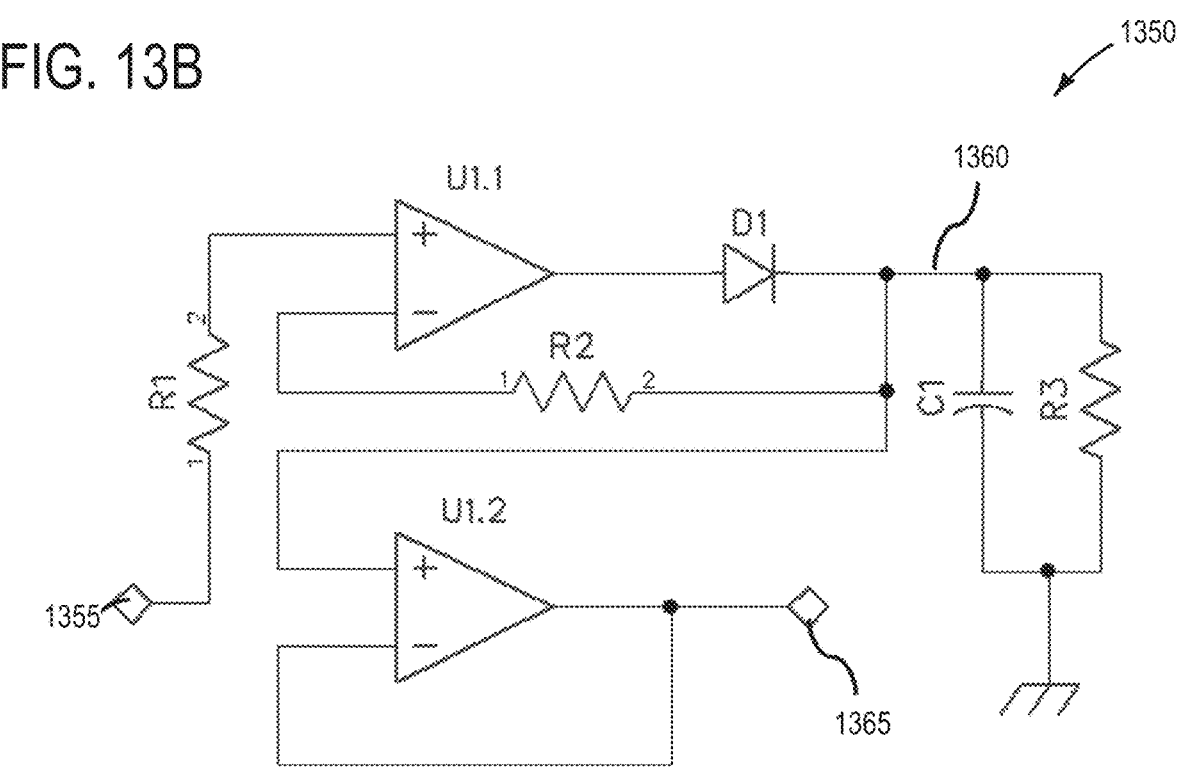
FIG. 13B depicts a schematic diagram of audio detection circuitry of the embodiment of FIG. 9.

Received audio from a portable radio (e.g. 2) via adapter module radio interface connector 1240 may be continuously routed via audio routing switch 1222 to a received audio detector 1225, and then to an input pin of microprocessor 1203, which may enable a determination as to whether there is active radio traffic on a particular channel. Circuitry of received audio detector 1225 is depicted at FIG. 13B.

By monitoring each of the push-to-talk line (e.g. 1242) and received audio (e.g. via 1240) of the portable radio (e.g. 2), microprocessor 1203 may detect if the portable radio is in use for transmission, or if an incoming message is being received. In this way, microprocessor 1203 may implement a radio discipline which may delay any local or transmitted announcements until there is a period of no outbound and/or inbound radio traffic.

Figure 15:
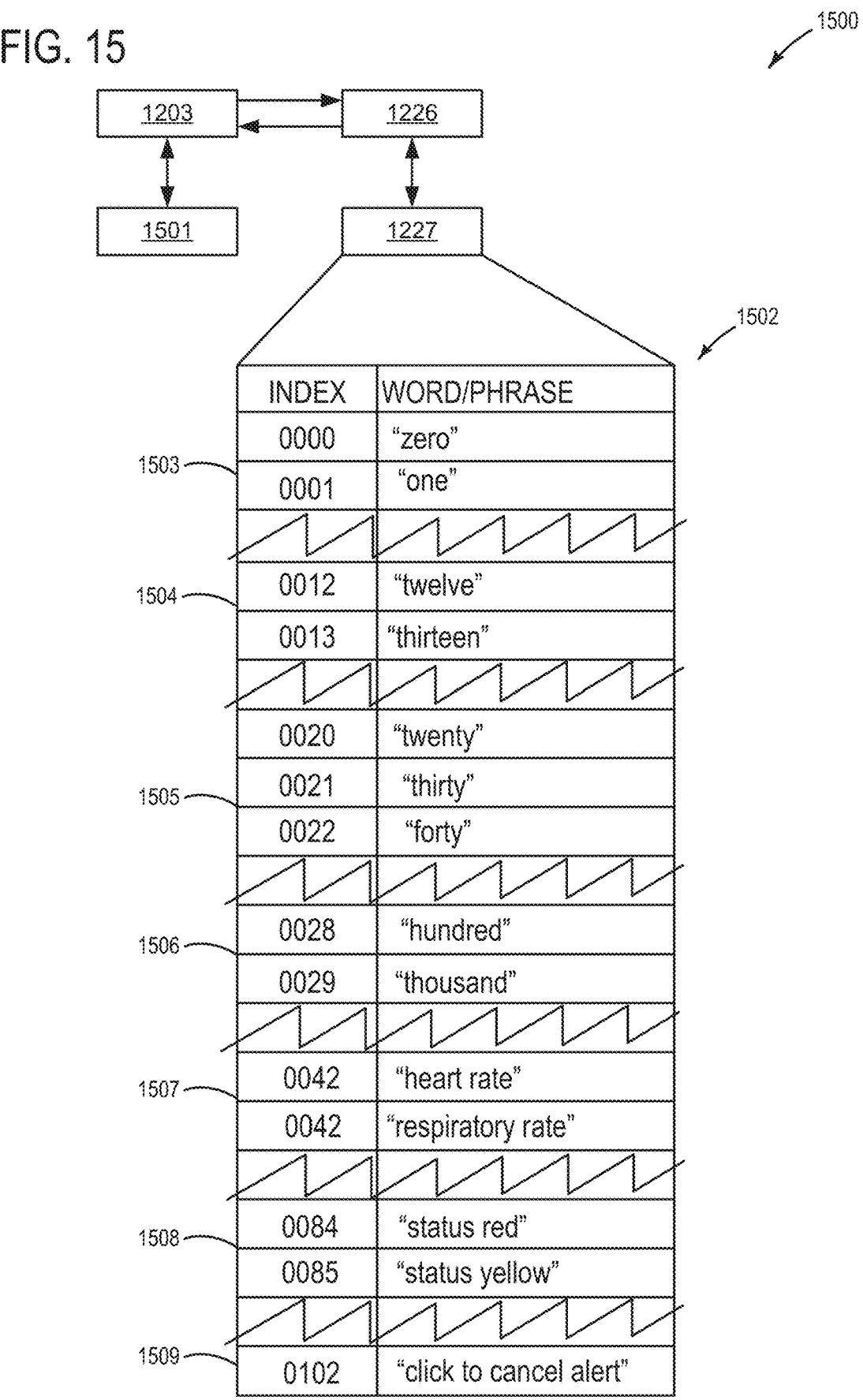
FIG. 15 depicts an example of how a voice announcement is composed, as used via the method of FIG. 14.

Key words, numbers, and/or phrases corresponding to voice announcements may be stored as audio files in a compressed format (e.g. MP3, OGG) in order to reduce memory requirements in audio file memory 1227 and/or in shared program and data memory 1204. To generate an announcement, microprocessor 1203 may assemble a sequence of appropriate files (as shown in FIG. 15), and may then route said files to an audio file decoder and amplifier 1226.

For a local announcement, microprocessor 1203 may activate audio routing switch 1222 to connect an output of audio file decoder and amplifier 1226 to loudspeaker 1223, overriding a normal or usual connection from portable radio to loudspeaker 1223. Microprocessor 1203 may prepare a word/phrase list that composes the announcement, and may request playback of each word/phrase in audio file memory 1227 via audio file decoder and amplifier 1226. However, microprocessor 1203 may continue to monitor an audio output of the portable radio (e.g. 2) at adapter module radio interface connector 1240, and may interrupt the local announcement by deactivating audio routing switch 1222 immediately for any incoming traffic on the portable radio.

For a transmitted announcement, the microprocessor 1203 may activate audio routing switch 1222 to connect the output of audio file decoder and amplifier 1226 to loudspeaker 1223, but may also direct audio routing switch 1222 to connect an attenuated version of an announcement audio signal to a microphone input (e.g. 1244) of the portable radio (e.g. 2) at adapter module radio interface connector 1240. The microprocessor 1203 may simultaneously activate the push-to-talk line 1242 of the portable radio, to transmit/broadcast a voice announcement.

A plurality of components in FIGS. 12A and 12B are shared between the two embodiments of the alerting device (e.g. 101). It will be understood that shared components between FIGS. 12A and 12B function in a substantially similar manner to one another, unless otherwise noted. Accordingly, the description provided below in reference to FIG. 12B is limited to deviations from FIG. 12A. Turning now to FIG. 12B, it depicts an example block diagram 1250 of electronic circuitry within the MS module (e.g. 905), as well as an interface with the portable radio (e.g. 2). Components specific to the MS module include similar features to components present in the RSM (e.g. 3), which in the embodiment of FIG. 12A may be interfaced to the portable radio (e.g. 2) via the adapter module (e.g. 205). However, since such features are integrated within the MS module, no adapter module RSM connector (e.g. 1230) is included at FIG. 12B, and the radio interface connector is referred to as MS module radio interface connector 1249 (e.g. same as 922). However, as discussed above with regard to FIGS. 9B-9C, it may be understood that the MS module radio interface connector may be substantially similar to the adapter module radio interface connector, aside from the fact that the radio interface connector associated with the adapter module is coupled to the adapter module whereas the radio interface connector associated with the MS module couples to MS module.

A push-to-talk switch, or actuator, 1251 may connect to microprocessor 1203 and each of a loudspeaker 1253 and microphone 1254 may connect to audio routing switch 1222. Further, status-check switch 1210 may be sensed via an input pin of microprocessor 1203, and an illuminating LED within switch 1210 may be controlled by an output pin of microprocessor 1203. Radio push-to-talk line 1242 from the portable radio may be connected via MS module radio interface connector 1249, and may also be connected to input/output pins on microprocessor 1203 via circuitry (as shown in FIG. 13A) that prevents situations where an exhausted battery in the MS module pulls a push-to-talk line (e.g. 1251) to ground and falsely initiates a transmission. Status LEDs 1280, for example first, second, and third signal lights (e.g. 910, 911, and 912, respectively), may be implemented as separate and discrete elements, rather than integrated into one component. In this way, both LED color (e.g. green, yellow, red) and relative position with respect to each of status LEDs 1212 may serve to communicate a current stress status of an individual wearing the MS module. It may be understood that status LEDs 1280 may be of a lower brightness than status LEDs 1212 in some examples. However, in other examples status LEDs 1280 may be of a similar brightness as compared to status LEDs 1212.

Turning to FIG. 13A, an example circuit diagram 1300 depicts details of circuitry connecting a MS module (e.g. 905) to a push-to-talk line 1305 of a portable radio (e.g. 2). The push-to-talk line 1305 may be connected through a diode D1 to an input pin 1306 of a microprocessor (e.g. 1203). Push-to-talk line 1305 may be normally biased to a logic high state by the portable radio (e.g. 2). When a push-to-talk actuator (e.g. 930) is actuated, push-to-talk line 1305 may be connected to ground, and input pin 1306 may likewise be pulled to a logic low state because of conduction in diode D1. In an event that a MS module battery is exhausted and the microprocessor powers down, input pin 1306 may be prevented from pulling down push-to-talk line 1305 by a reverse state of diode D1.

An output pin 1310 of the microprocessor (e.g. 1203) may control the gate of an N-channel MOSFET transistor Q1. To activate a push-to-talk circuit for a radio announcement, output pin 1310 may be driven to a logic high state, causing Q1 to conduct and driving push-to-talk line 1305 to a low state, activating the portable radio (e.g. 2). In an event that the microprocessor is powered down, resistor R1 may ensure Q1 is turned off even without output pin 1310 in a high impedance state.

Turning to FIG. 13B, a partial schematic diagram 1350 depicts received audio detection circuitry of a MS module (e.g. 905). A received audio signal 1355 from a portable radio (e.g. 2) may be amplified by operational amplifier U1.1 with an ideal diode negative feedback loop which ensures small signal voltages, which may be below a forward conduction drop of a diode D1, are detected and rectified, appearing on output line 1360. Due to low output impedance of U1.1, capacitor C1 may be charged immediately by peaks in received audio signal 1355, while a decay time may be much slower, set by a time constant of C1 with resistor R3. A detected voltage may be buffered by a unity-gain operational amplifier U1.2, in some examples integrated with U1.1 in a single integrated circuit, and a buffered output 1365 may be routed to an analog input pin of a microprocessor (e.g. 1203). The time constant of C1 and R3 may be set to be several seconds to provide a nominal delay after received audio signal 1355 has ended before the MS module begins an announcement.

Figure 14:
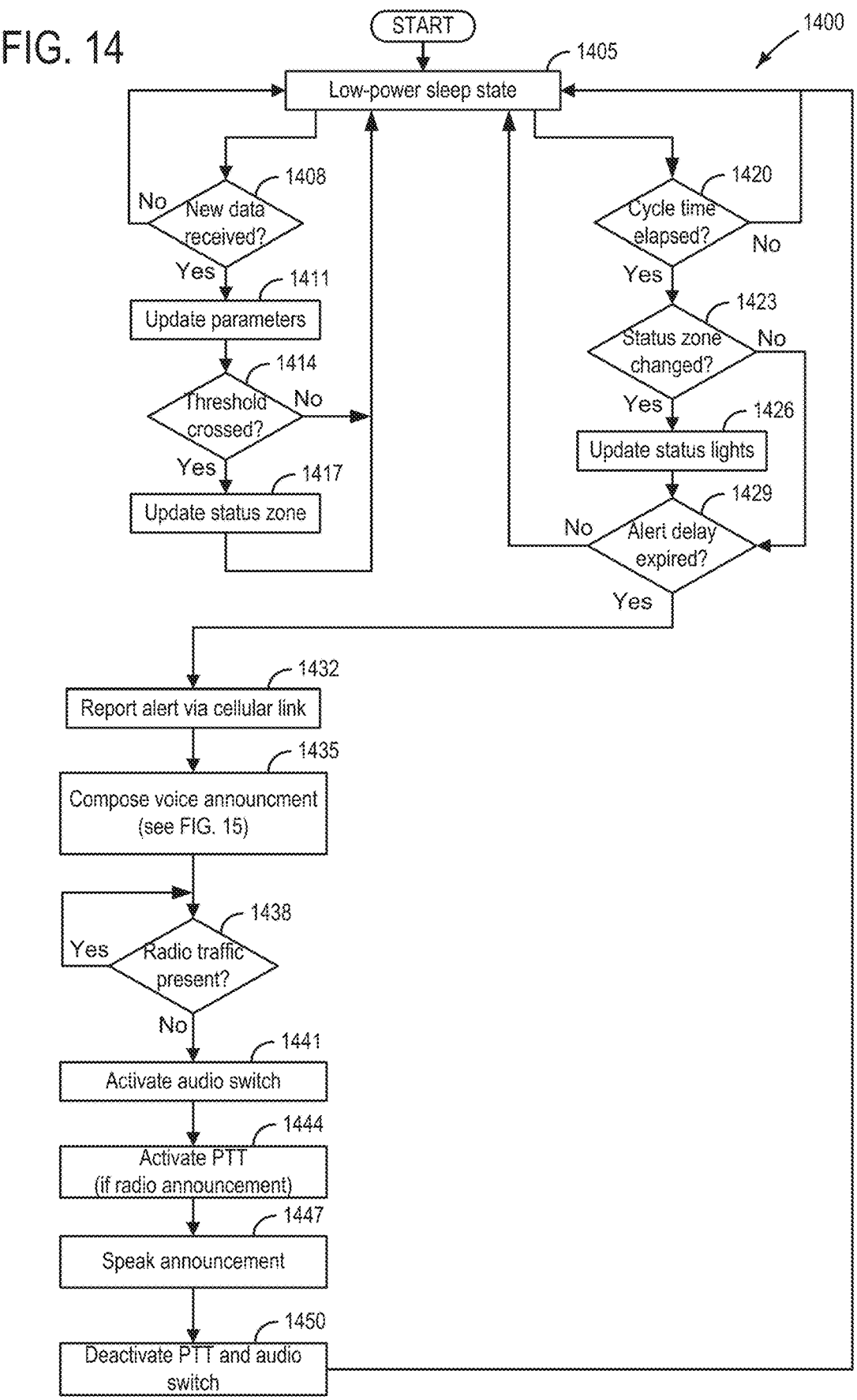
FIG. 14 depicts an example method for use with one or more of the embodiments of FIGS. 2A-2B and FIG. 9A.

Turning to FIG. 14, an example method 1400 is depicted, illustrating steps involved in operation of an adapter (e.g. 205) and/or MS module (e.g. 905). Method 1400 will be described with reference to the systems described herein, though it may be understood that similar methods may be applied to other systems without departing from the scope of this disclosure. Method steps depicted at FIG. 14 may be carried out via a controller (e.g. 1209), and may be stored at the controller as executable instructions in non-transitory memory. Instructions for carrying out method 1400 may be executed by the controller based on instructions stored on a memory of the controller and in conjunction with signals received from one or more sensors (e.g. 102). The controller may employ actuators to change status of various components described herein.

At 1405, the controller (e.g. 1209) of the adapter (e.g. 205) and/or MS module (e.g. 905) is in a low-power sleep state in order to conserve battery energy. In response to new data being received from a wearable sensor (e.g. 102) at 1408 via a low-power radio transceiver (e.g. 1205), method 1400 may proceed to 1411 where the controller is woken up in order to process the new data. The new data may comprise physiological data related to a wearer of the wearable sensor and/or environmental data as monitored via the wearable sensor. At 1411, method 1400 may include updating parameters of one or more of the physiological and/or environmental data in response to the new data. The updated parameters may be stored at the memory of the controller (e.g. 1204).

Proceeding to 1414, method 1400 may include indicating whether a threshold has been crossed due to the new data and updated parameters. The threshold may comprise a personalized threshold, as discussed above. There may be a plurality of thresholds, for example a first threshold and a second threshold. When below the first threshold, it may be understood that the wearer of the adapter (e.g. 205) and/or MS module (e.g. 905) may be in a safe zone. The safe zone may comprise a status zone where physical activity/exertion levels, and optionally environmental parameters, are such that a potential adverse health event is unlikely unless conditions change. When above the first threshold but below the second threshold, it may be understood that the wearer of the adapter and/or MS module may be in an intermediate zone. The intermediate zone may comprise a status zone where there is a greater risk of an adverse health event to the wearer of the adapter and/or MS module than when the wearer of the adapter is in the safe zone (below the first threshold). When above the second threshold, it may be understood that the wearer of the adapter and/or MS module is in a dangerous zone, where an adverse health event may be likely if mitigating action is not quickly taken to remove the wearer of the adapter and/or MS module from a current situation.

Thus, at 1414, if the new data received results in updated parameters such that a threshold is indicated to be crossed (either from a lower zone such as the safe zone to a higher zone such as the intermediate zone, or from the a higher zone such as the intermediate zone to a lower zone such as the safe zone), then method 1400 may proceed to 1417. Alternatively, if the new data received does not result in a threshold being crossed, then method 1400 may return to 1405, where the controller (e.g. 1209) is returned to the low-power sleep state.

Returning to 1414, in response to an indication that a threshold has been crossed, method 1400 proceeds to 1417 where the status zone is updated. As an example, the status zone may be updated to the dangerous zone in response to the second threshold being crossed as a result of the new data received.

Once the status zone has been updated and stored at the controller (e.g. 1209), the controller may return to 1405 where the controller is returned to the low-power sleep state.

The controller (e.g. 1209) will also wake up from the low-power sleep state upon expiration of a cycle timer at 1420, to determine whether the status zone has changed since a last time the controller was woken up. A cycle time may comprise 5 seconds, for example, but may be less than 5 seconds or greater than 5 seconds without departing from the scope of this disclosure.

If at 1420 the cycle time has not elapsed, method 1400 may return to 1405 where the controller (e.g. 1209) is maintained in the low-power sleep state. Alternatively, responsive to the cycle time elapsing at 1420, method 1400 may proceed to 1423. At 1423, method 1400 may query as to whether the status zone has changed. If so, then method 1400 may proceed to 1426. At 1426, method 1400 may include updating status lights of the adapter (e.g. 205) and/or MS module (e.g. 905). For example, updating status lights of the adapter and/or MS module may include changing a color of a projecting light (e.g. 430).

More specifically, in a situation where a particular firefighter/first responder is indicated to have crossed into the intermediate zone from the safe zone, at 1426 method 1400 may include illuminating the projecting signal light yellow, rather than green, where the particular firefighter/first responder is wearing the adapter module (e.g. 205). Alternatively, in an example where the particular firefighter/first responder is wearing the MS module (e.g. 905), then a second signal light (e.g. 911) may be illuminated yellow, and a first signal light (e.g. 910) may not be illuminated.

Proceeding to 1429, method 1400 may include indicating whether an alert delay period has expired. More specifically, at 1429, method 1400 may include indicating a duration that the firefighter/first responder has been in a particular status zone. The duration may be compared to a preset delay period. If the delay period has not expired at 1429, then method 1400 may return to 1405 where the controller (e.g. 1209) may return to the low-power sleep state.

Alternatively, in response to an indication that the delay period has expired at 1429, method 1400 may proceed to 1432. At 1432, method 1400 may include issuing an alert via the transceiver (e.g. 1206; where included).

Proceeding to 1435, method 1400 may include composing a voice announcement. Exemplary methodology for composing such a voice announcement is discussed in detail below in reference to FIG. 15.

Proceeding to 1438, method 1400 may include determining whether radio traffic (both inbound and outbound) is present for the particular channel. If it is indicated at 1438 that radio traffic is present, then the controller (e.g. 1209) may postpone any alert until there is an absence of radio traffic.

In response to an indication of an absence of radio traffic at 1438, method 1400 may proceed to 1441. At 1441, method 1400 may include activating an audio switch (e.g. 1222). If the announcement is to be transmitted over a radio, such as the portable radio (e.g. 2), then a push-to-talk (PTT) switch, or actuator, (e.g. 1221) may be activated at 1444. Proceeding to 1447, method 1400 may include speaking the announcement (as shown in FIG. 15 for further details). Following the announcement being spoken, at 1450, method 1400 may include deactivating the PTT switch and/or the audio switch, whereupon the controller (e.g. 1209) may be returned to the low-power sleep mode at 1405.

Turning now to FIG. 15, an example illustration 1500 is depicted, illustrating how a voice announcement may be composed/synthesized once a request for such an announcement has been initiated. More specifically, returning to the methodology depicted at FIG. 14, at step 1435, method 1400 included composing a voice announcement. Thus, a methodology depicted at FIG. 15 shows in further detail how such a voice announcement is composed.

Microprocessor 1203 may assemble the announcement in a word/phrase queue 1501 by using word/phrase components that have been pre-recorded as compressed audio files and stored in audio file memory 1227. Microprocessor 1203 may then request playback of a first audio file in word/phrase queue 1501 via audio file decoder and amplifier 1226. An interrupt signal may be signaled back as soon as playback of a first audio file is complete, such that a next (e.g. second) word may be requested to be played back, and so on until queue 1501 is empty.

Examples of the contents of audio file memory 1227 are depicted at table 1502. Each entry in audio file memory has an index number and compressed audio for a particular word/phrase. For example, single-digit numbers "zero" through "nine" may occupy the first ten slots at 1503 (only slots for "zero" and "one" are depicted for clarity, and similar abbreviation of the table applies to examples below).

Numbers "ten" through "nineteen" may occupy the next ten slots at 1504. Beyond the ten slots at 1504, eight more slots 1505 may be used to represent numbers "twenty" through "ninety". Two more slots at 1506 may be used for "hundred" and "thousand." Microprocessor 1203 may thus announce any number from 0 to 999,999 by composing them from one or more of thirty audio files. Other audio files may relate to physiological and/or environmental parameters such as "heart rate" or "respiratory rate" at 1507, status color alerts such as "status red" or "status yellow" at 1508, and other instructional messages such as "click to cancel alert" at 1509.

As an example, an alert announcement may comprise "Unit 51 alpha, status red, duration five minutes." As another example, a manual request via the status check actuator (e.g. 210) may produce an alert announcement "Unit 41 delta, status yellow, heart rate 140." In this way, less than a particular threshold (e.g. 200) number of words/phrases may cover all desired options for alert announcements. Such word/phrase audio files may be compressed as MP3 format such that a small amount of megabytes (e.g. less than 2) of data may support all desired options for alert announcements, where the small amount may easily be accommodated in a flash memory chip.

Figure 16:
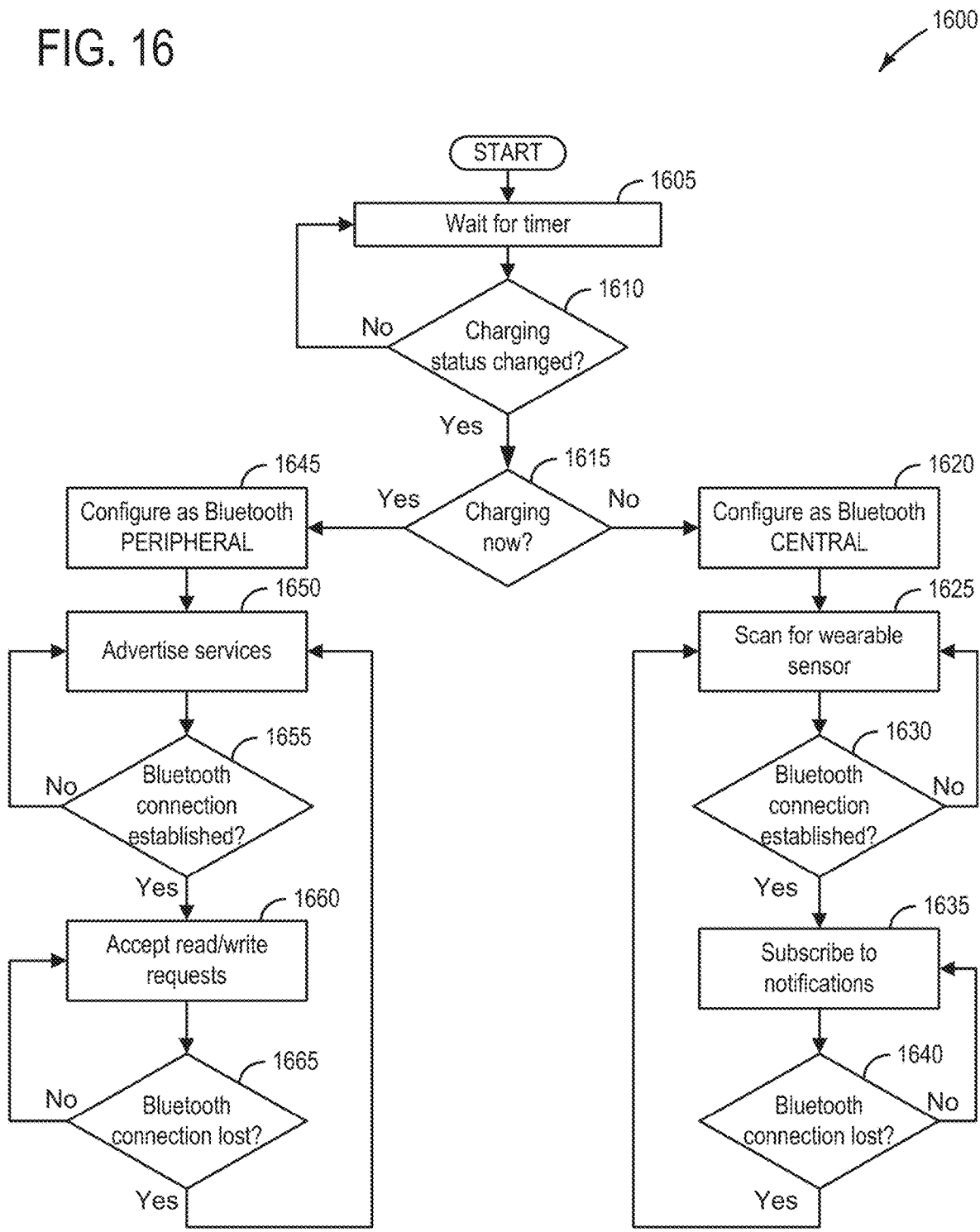
FIG. 16 depicts an example methodology for controlling operating modes of a low-power transceiver discussed at FIG. 12, for use with one or more of the embodiments of FIGS. 2A-2B and FIG. 9A.

Turning now to FIG. 16, it depicts an example method 1600 for controlling operating modes of a low-power radio transceiver (e.g. 1205), for use with an adapter (e.g. 205) and/or MS module (e.g. 905). Specifically, at 1605, method 1600 may include waiting for a timer associated with the low-power radio transceiver to expire. For example, the timer may be configured to trigger every 5 seconds (although the trigger may be greater than or less than 5 seconds without departing from the scope of this disclosure), at which point method 1600 may proceed to 1610. At 1610, method 1600 may include determining whether a charging status for a battery (e.g. 1201) of the adapter and/or MS module has changed. If not, then method 1600 may return to 1605. Alternatively, in response to an indication that the charging status has changed at 1610, method 1600 may proceed to 1615. At 1615, method 1600 may include indicating whether a change in charging status reflects an indication that the battery associated with the adapter and/or MS module is currently charging or not. If not, method 1600 may proceed to 1620. At 1620, method 1600 may include configuring the low-power radio transceiver as a central device, corresponding to in-field usage. Accordingly, proceeding to 1625, method 1600 may include the low-power radio transceiver scanning for a signal from a wearable sensor (e.g. 102). Accordingly, proceeding to 1630, method 1600 may include indicating whether a wireless connection (e.g. via Bluetooth technology) is established between the wearable sensor and the low-power radio transceiver. In other examples not depicted, other forms of wireless connection may be implemented. If not, method 1600 may return to 1625 where the scanning may continue.

Alternatively, responsive to an indication that the wireless connection has been established between the wearable sensor (e.g. 102) and the low-power radio transceiver (e.g. 1205), method 1600 may proceed to 1635. At 1635, method 1600 may include subscribing to notifications. By subscribing to notifications, it may be understood that the low-power radio transceiver may receive periodic updates from the wearable sensor. Such updates may be processed as discussed above with regard to FIG. 14. Proceeding to 1640, in response to the wireless connection being lost, method 1600 may return to 1625, where method 1600 may once again scan for the wearable sensor to re-establish the connection.

Returning to 1615, in response to an indication that the battery (e.g. 1201) associated with the adapter (e.g. 205) and/or MS module (e.g. 905) is currently charging, method 1600 may proceed to 1645. At 1645, method 1600 may include configuring the low-power radio transceiver (e.g. 1205) as a peripheral device (e.g. Bluetooth peripheral device). It may be understood that configuration in a peripheral mode may correspond to administrative usage at a first responder base location, for example. In response to being configured in the peripheral mode at 1645, method 1600 may proceed to 1650. At 1650, method 1600 may include advertising services. Accordingly, proceeding to 1655, method 1600 may include indicating whether the stress management application (e.g. 103, as discussed in further detail below in reference to FIGS. 17A-20) has requested and established a wireless connection to the low-power radio transceiver. If not, method 1600 may return to 1650, where services may continue to be advertised. Alternatively, in response to the wireless connection being established at 1655, method 1600 may proceed to 1660. At 1660, method 1600 may include accepting attribute read and write requests to synchronize settings, preferences, and stored data with the stress management application. In this way, personalized thresholds for alerts may be established, as one example.

Proceeding to 1665, method 1600 may include indicating whether the wireless connection is lost. If not, method 1600 may continue to accept read/write requests at 1660. In response to the wireless connection being lost, method 1600 may return to 1650, where the low-power radio transceiver (e.g. 1205) may once again advertise services.

All the while, it may be understood that the timer discussed at 1605 may continue to trigger a query as to whether the charging status has changed, whereupon method 1600 may proceed accordingly, as discussed in detail above.

Turning now to FIGS. 17A-21B, they depict example embodiments of a device management application (such as stress management application 103, as discussed in reference to FIG. 1) running on a mobile device (such as computing device 13, as discussed in reference to FIG. 1), which as discussed above may be used to synchronize settings, preferences, and/or stored data with a low-power radio transceiver (e.g. 1205) associated with an adapter (e.g. 205) and/or MS module (e.g. 905). In some examples, the stored data may be a database including physiological and/or environmental parameter history, personalized settings/parameters, etc., for each of a plurality of firefighters/first responders.

Figure 17B:
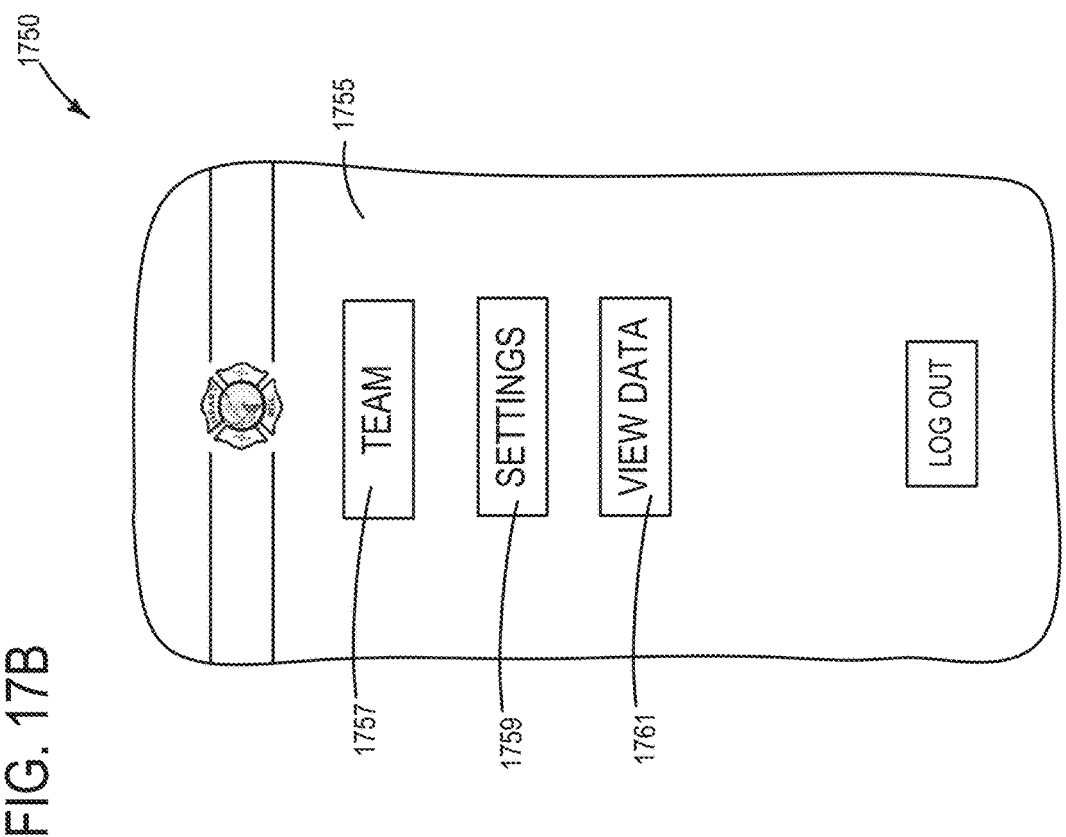
FIGS. 17A-20 depict example embodiments of a stress management application, for use with one or more of the embodiments of FIGS. 2A-2B and FIG. 9A.
Figure 17A:
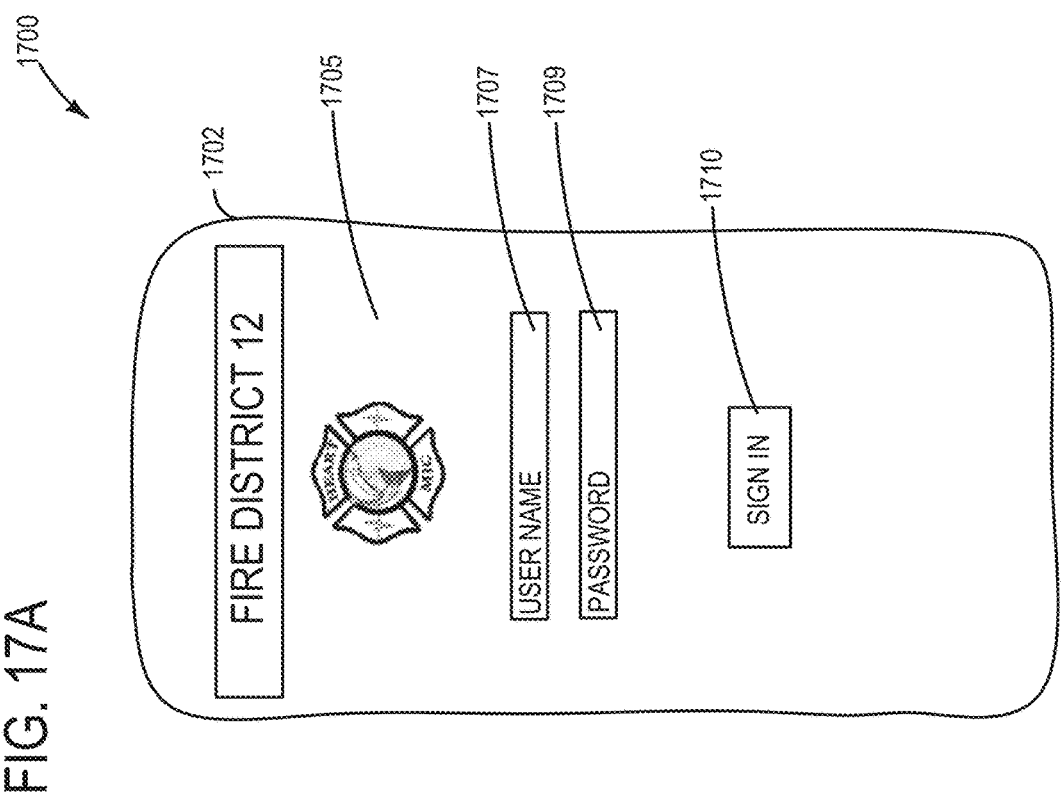

FIG. 17A depicts an example illustration 1700 of an embodiment of the stress management application running on a smartphone 1702. A log-in screen 1705 may request entry of a user name 1707, and a password 1709. Upon entering correct user name and password information, a user of the stress management application may sign in 1710.

Turning to FIG. 17B, depicted is an example illustration 1750 of a screen display of a main menu 1755 of the stress management application, which may allow for selection items including one or more team members 1757, settings 1759 (for example, various settings may be changed/updated), or for reviewing physiological and/or environmental data 1761 that has been recorded, for example, via a wearable sensor (e.g. 102).

Figure 18A:
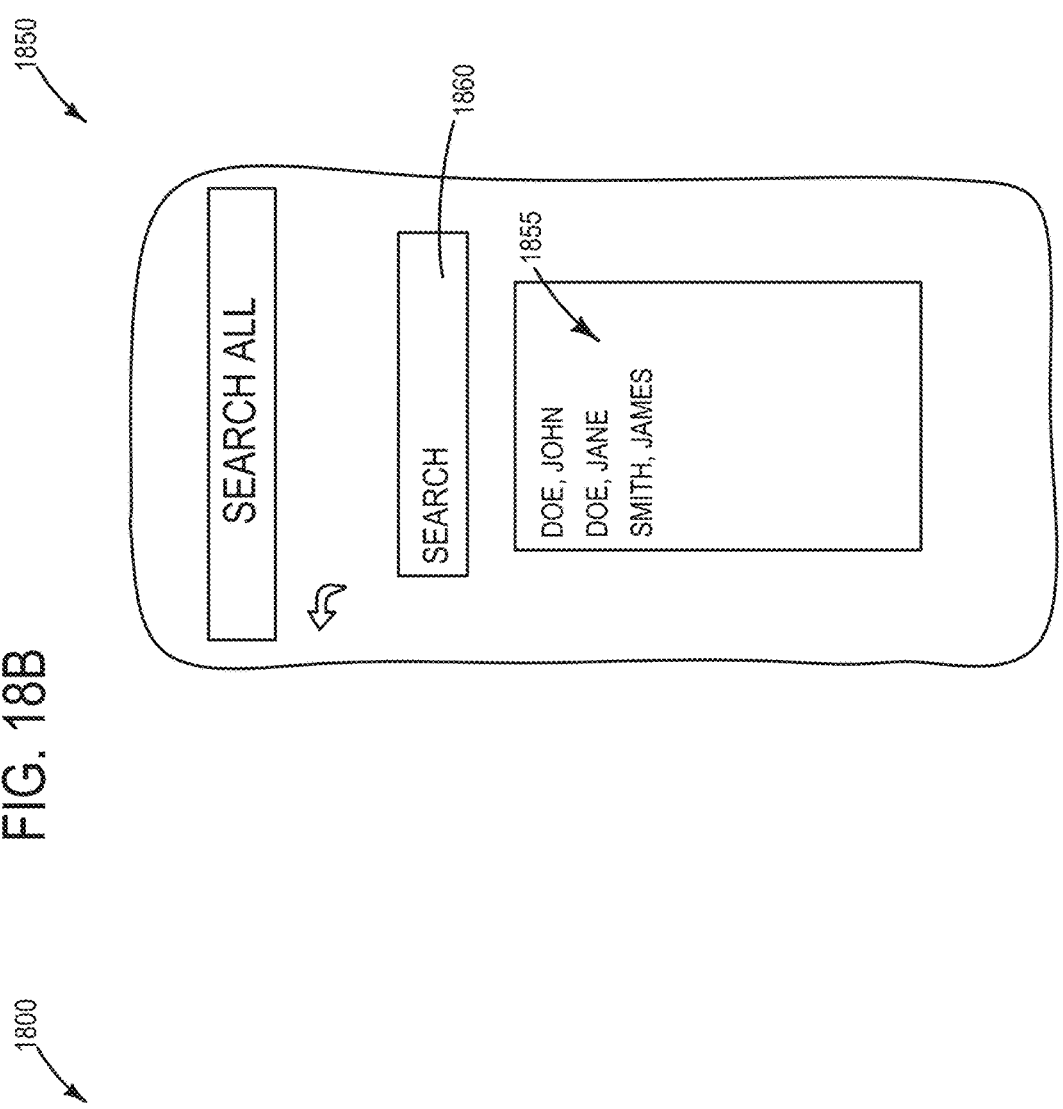

Turning to FIG. 18A, depicted is an example illustration 1800 of a filtering mechanism 1805 for selecting one or more particular team members. The filtering mechanism may allow for selecting the one or more team members by shift (e.g. shift A, shift B, etc.), or by station (e.g. station 61, station 62, etc.).

Figure 18B:
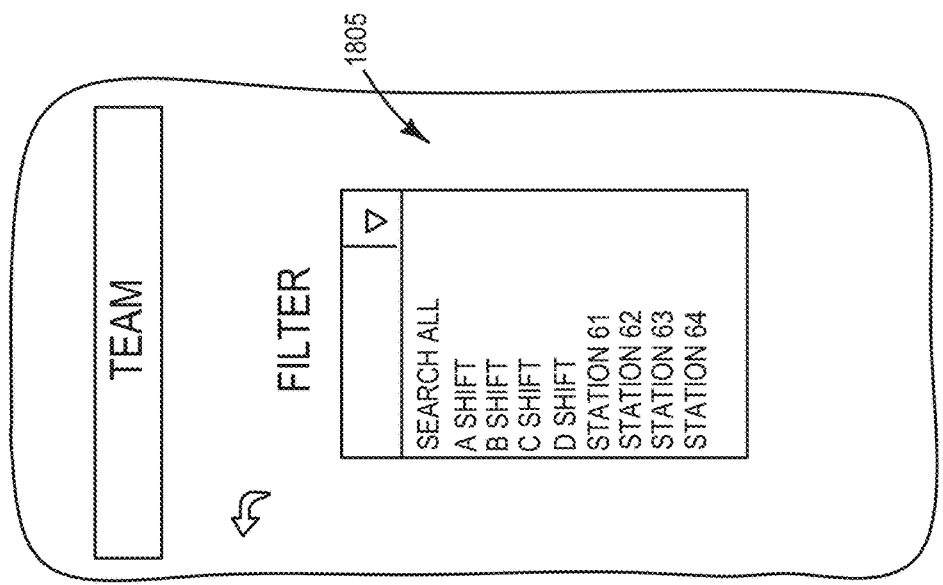

Turning to FIG. 18B, depicted is an example illustration 1850, illustrating one example embodiment of the stress management application which may allow for the user of the stress management application to select one or more team members by name 1855, and then get information on said one or more team members via a search input 1860.

Figure 19:
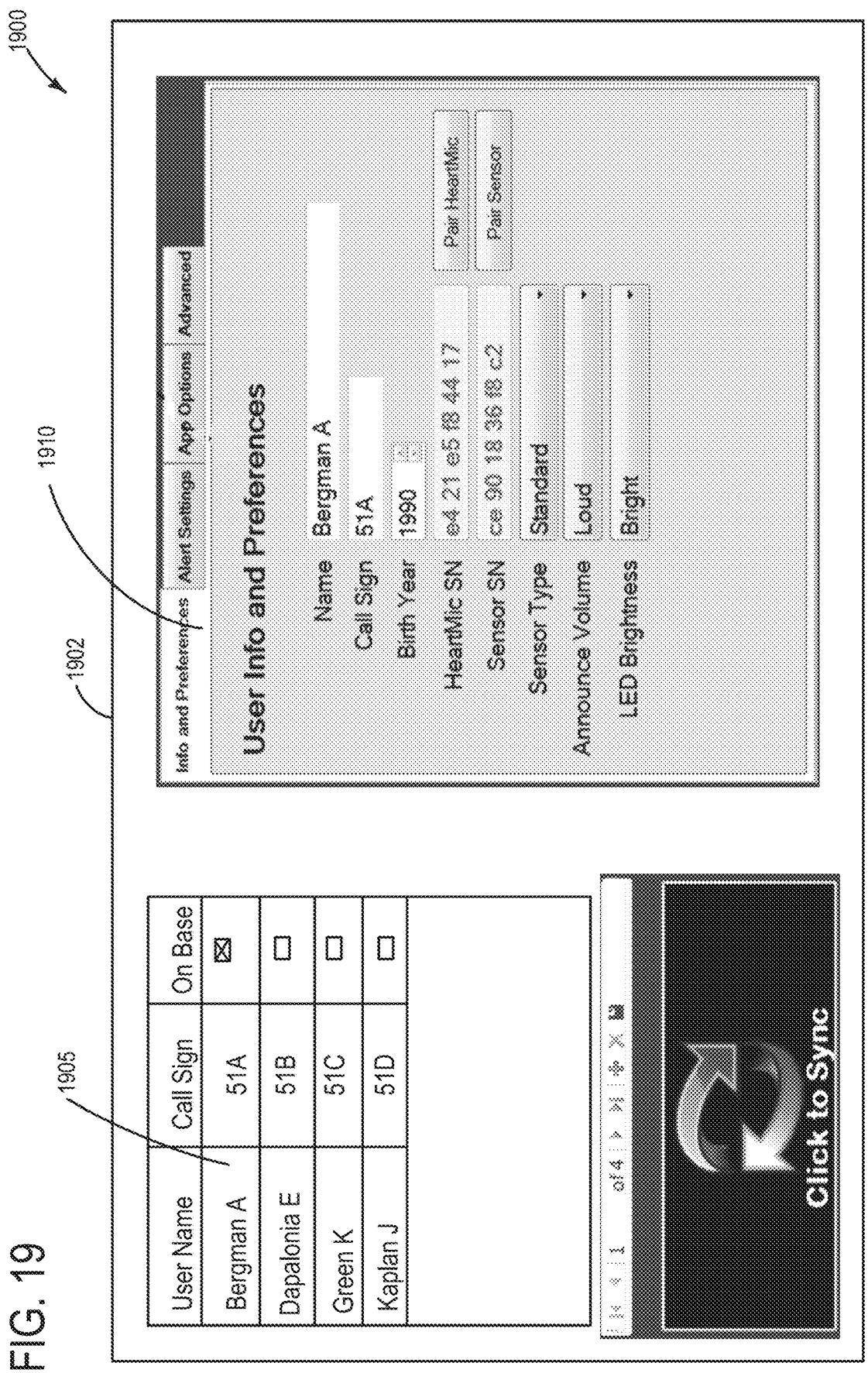

Turning now to FIG. 19, it depicts an example illustration 1900 of an embodiment of the stress management application running on the mobile device (e.g. mobile data terminal, tablet, laptop, smartphone, etc.). An information and preferences screen 1902 may include a list of team members 1905. Upon selecting a team member (e.g. "Bergman A" in example illustration 1900), information and preferences 1910 for said team member may be reviewed and edited. As depicted at FIG. 19, examples of information and preferences may include name, call sign, birth year (for age calculation), hardware identifying information for the adapter (e.g. 205) and/or MS module (e.g. 905), preferred volume for local announcements (where applicable), and brightness level for adapter signal lights (e.g. 215) and/or MS module signal lights (e.g. 908).

Figure 20:
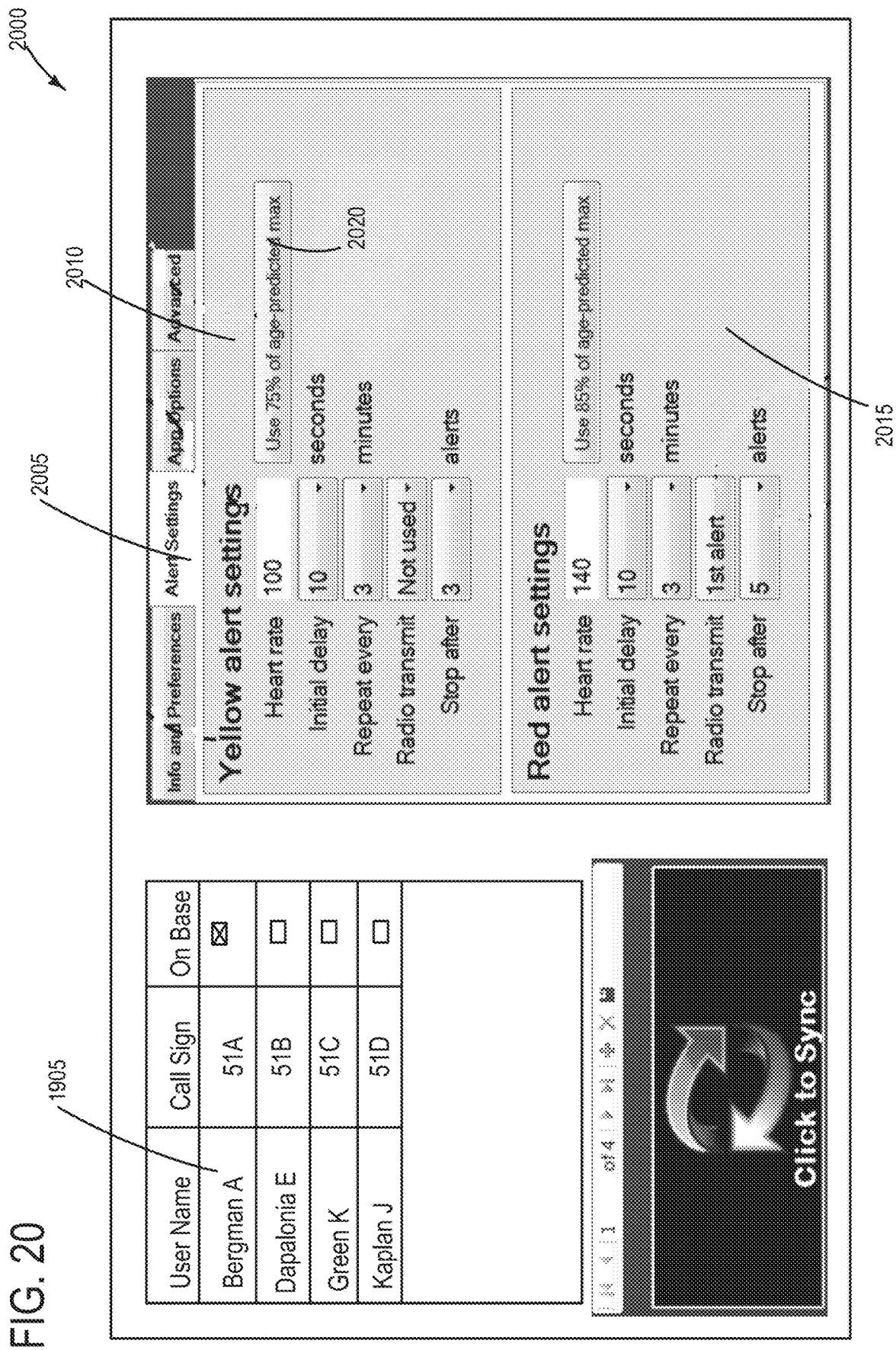

Turning now to FIG. 20, depicted is an example illustration 2000 of an example selection screen of the stress management application. The team member selection list 1905 is retained from an information and preferences screen (e.g. 1910), and an alert settings screen 2005 is displayed. Depicted at FIG. 20 is both a settings section for a yellow alert 2010 and a red alert 2015. For each of the two alert levels a heart rate threshold may be input manually, or may be automatically calculated based on an age of a particular selected team member, via selection link 2020. An initial delay before an announcement is made may be entered, and a repetition interval between alerts may be set as well for each alert (yellow and red).

Figure 21A:
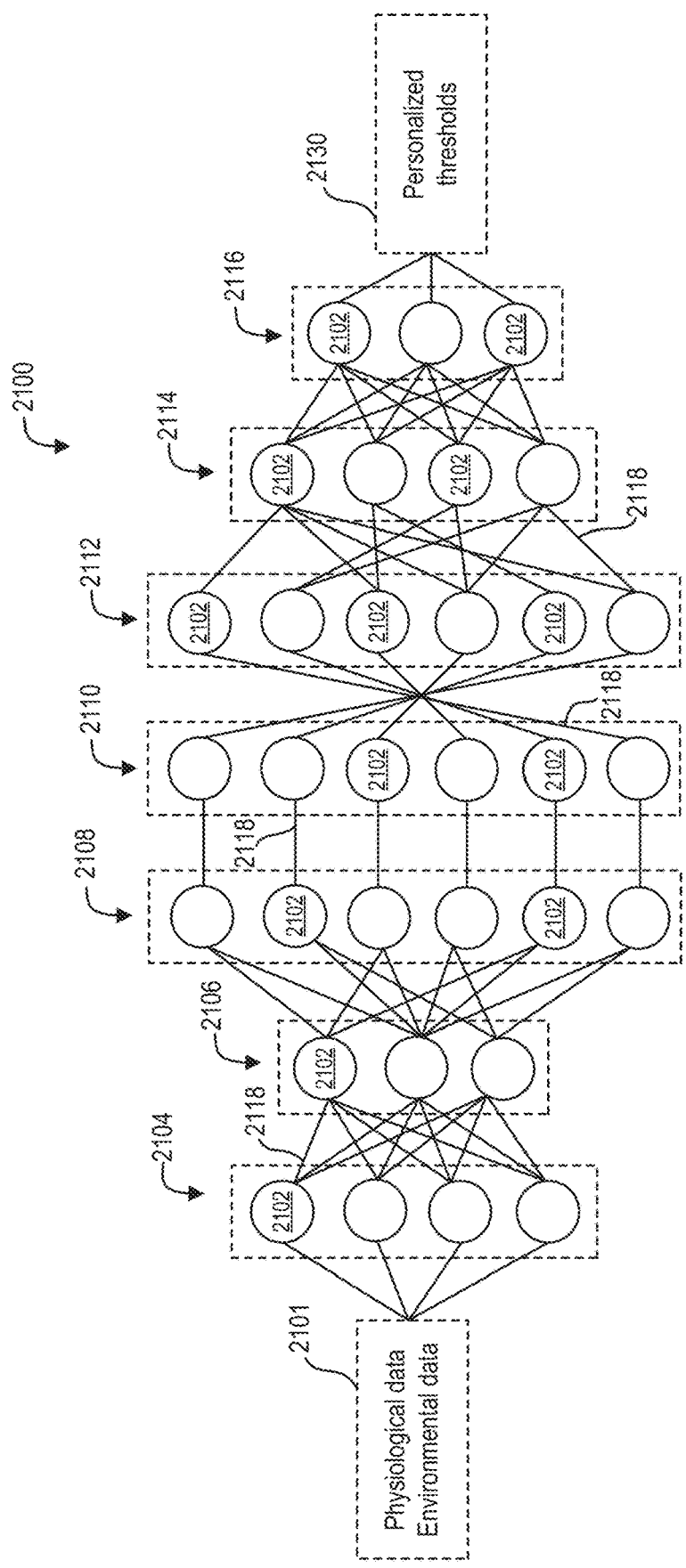
FIG. 21A depicts a schematic diagram illustrating an example neural network.

In some examples, an analytics module (e.g. 14) may employ a machine learning, or deep learning, or data mining, methodology to periodically update personalized thresholds for evaluating a potential adverse health event for a firefighter or first responder. Machine learning methods may include but are not limited to linear regression, logistic regression, elastic nets, singular value decomposition, restricted Boltzmann machines, Markov chains, latent dirichlet allocation, association rules, gradient boosted decision trees, random forests, clustering techniques, and/or matrix factorization. As such, the personalized thresholds may dynamically account for fluctuating trends in physiological and/or environmental factors as experienced by said firefighter or first responder. As an illustrative example, FIG. 21A depicts a neural network 2100 having one or more nodes/neurons 2102 which, in some embodiments, may be disposed into one or more layers 2104, 2106, 2108, 2110, 2112, 2114, and 2116. Neural network 2100 may be a deep neural network. As used herein with respect to neurons, the term "layer" refers to a collection of simulated neurons that have inputs and/or outputs connected in similar fashion to other collections of simulated neurons. Accordingly, as show in FIG. 21A, neurons 2102 may be connected to each other via one or more connections 2118 such that data may propagate from an input layer 2104, through one or more intermediate layers 2106, 2108, 2110, 2112, and 2114, to an output layer 2116.

Figure 21B:
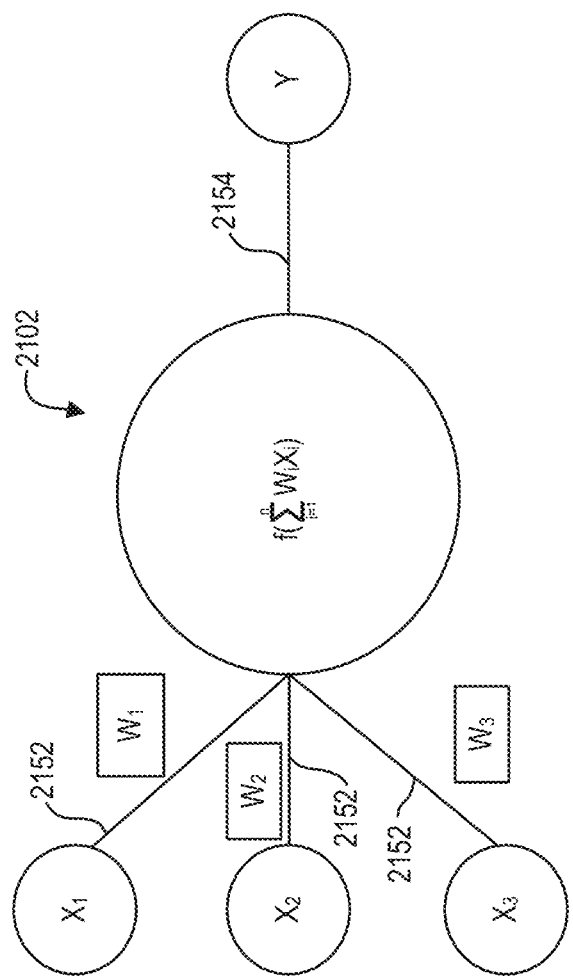
FIG. 21B depicts a schematic diagram illustrating an example node of the neural network.

FIG. 21B shows input and output connections for a neuron in accordance with an exemplary embodiment. As shown in FIG. 21B, connections 2118 of an individual neuron 2102 may include one or more input connections 2152 and one or more output connections 2154. Each input connection 2152 of neuron 2102 may be an output connection of a preceding neuron, and each output connection 2154 of neuron 2102 may be an input connection of one or more subsequent neurons. While FIG. 21B depicts neuron 2102 as having a single output connection 2154, it should be understood that neurons may have multiple output connections that send/transmit/pass the same value. In some embodiments, neurons 2102 may be data constructs (e.g. structures, instantiated class objects, matrices, etc.) and input connections 2118 may be received by neuron 2102 as weighted numerical values (e.g. floating point or integer values). For example, as further shown in FIG. 21B, input connections $X_1$, $X_2$, and $X_3$ may be weighted via weights $W_1$, $W_2$, and $W_3$, respectively, summed, and sent/transmitted/passed as output connection Y. As will be appreciated, the processing of an individual neuron 2102 may be represented generally by the equation:

$$Y = f\left(\sum_{i=1}^{n} W_i X_i\right)$$

where n is the total number of input connections 2152 to neuron 2102. In one embodiment, the value of Y may be based at least in part on whether the summation of $W_i X_i$ exceeds a threshold. For example, Y may have a value of zero (0) if the summation of the weighted inputs fails to exceed a desired threshold.

As will be further understood, input connections 2152 of neurons 2102 in input layer 2104 may be mapped to an input 2101, while output connections 2154 of neurons 2102 in output layer 2116 may be mapped to an output 2130. As used herein, "mapping" a given input connection 2152 to input 2101 refers to the manner by which input 2101 affects/dictates the value said input connection 2102. Similarly, as also used herein, "mapping" a given output connection 2154 to output 2130 refers to the manner by which the value of said output connection 2154 affects/dictates output 2130.

Accordingly, in some embodiments, the acquired/obtained input 2101 is passed/fed to input layer 2104 of neural network 2100 and propagated through layers 2104, 2106, 2108, 2110, 2112, 2114, and 2116 such that mapped output connections 2154 of output layer 2116 generate/correspond to output 2130. As shown, input 2101 includes physiological and/or environmental data collected and subsequently transmitted by the wearable sensor (e.g. 102) on a given firefighter or first responder for a given time period. As depicted at FIG. 21A, output 2130 includes personalized thresholds, which may be accordingly updated via neural network 2100 as trends in physiological and/or environmental parameters evolve. In other examples, output 2130 may include settings and/or preferences for a stress management application (e.g. 103), such as alert delay periods, signal light sequence, etc.

Neural network 2100 may be trained using a plurality of training datasets. Each training dataset may include a plurality of incident intensity records, such as data or reports collected from past firefighting engagements, and/or a plurality of physiological and/or environmental parameters for a given firefighter or first responder. The physiological and/or environmental parameters may be collected since an initial use of the wearable sensor (e.g. 102) or since a most recent determination of personalized thresholds. In this way, neural network 2100 may utilize the plurality of training datasets to map updated physiological and/or environmental parameters (e.g. inputs) to updated personalized thresholds (e.g. outputs). The machine learning, or deep learning, therein (due to, for example, evolving trends in physiological and/or environmental parameters) may cause weights (e.g. $W_1$, $W_2$, and/or $W_3$) to change, input/output connections to change, or other adjustments to neural network 2100. As such, the sensitivity of an alerting system (e.g. 100) may be periodically increased, thereby improving resistance to false alerts ascribed to outdated or inaccurate information.

In this way, an alerting system may reduce risk of adverse health events for firefighters and/or first responders by alerting a given firefighter and/or first responder at risk, as well as other firefighters and/or first responders. A wearable sensor may transmit physiological and/or environmental data relevant to an accurate assessment of risk to the given firefighter and/or first responder to an alerting device. The alerting device may be operable to receive the data and may generate an alert if the alerting device determines that the data indicates that the given firefighter and/or first responder is experiencing a potential adverse health event based upon one or more personalized thresholds. The one or more personalized thresholds may be further based on a given environment or upon personal factors, and may be manually set on the alerting device. A technical effect of utilizing the one or more personalized thresholds in determining a potential adverse health event is that the generated alert may be specific to the given firefighter and/or first responder such that the risk to said firefighter and/or first responder may be more accurately and timely assessed. In some examples, the alerting device may be further operable to transmit the data to a cloud-based server, whereon the data may be stored. The alerting device and cloud-based server may be in further communication with a stress management application, whereon the data may be accessed and utilized to automatically and dynamically determine the one or more personalized thresholds, such as via machine learning. A technical effect of automatically and dynamically updating personalized thresholds is that accuracy and timely response to a potential adverse health event may be further improved based upon changing trends in physiological, environmental, and/or personal factors.

In one example, an alert system for reducing a risk of an adverse health event for a first responder comprises a wearable sensor and an alerting device, the alerting device capable to receive real-time data from the wearable sensor, the alerting device communicably coupled to an existing portable radio worn by the first responder, and wherein the alerting device issues a visual alert signal based on the real-time data received from the wearable sensor, the visual alert signal a function of one or more personalized thresholds related to a current level of stress that the first responder is experiencing.

In such a system, reducing the risk of the adverse health event may further comprise reducing a risk of sudden cardiac death.

In such a system, the wearable sensor may receive a collection of physiological data from the first responder. The one or more personalized threshold may be related to the physiological data. Additionally or alternatively, the wearable sensor may receive a collection of environmental data from the first responder. In such an example, the one or more personalized threshold may be related to the environmental data.

In such a system, the alerting device may further comprise an adapter module sandwiched between a remote speaker/microphone connector communicably coupled to an existing remote speaker/microphone, and the existing portable radio. The adapter module may include a high-brightness light source for issuing the visual alert signal.

In such a system, the alerting device may comprise a microphone/speaker module that replaces an existing remote speaker/microphone, where the microphone/speaker module is communicably coupled to the existing portable radio. The microphone/speaker module may include a first signal light, a second signal light, and a third signal light, and issuing the visual alert signal may include illuminating one of the first signal light, the second signal light, or the third signal light.

In such a system, the alerting device may harvest power from the existing portable radio.

In such a system, the alerting device may further comprise a transceiver for communicating the current level of stress that the first responder is experiencing to a cloud-based server.

In such a system, the system may further comprise a stress management application in wireless communication with the alerting device, wherein one or more settings of the alerting device that include at least the one or more personalized thresholds, may be set via the stress management application.

In such a system, the alerting device may further comprise a status check actuator that, when actuated, results in synthesis of a voice announcement related to the current level of stress that the first responder is experiencing, and wherein the status check actuator may be illuminated via a color of light different than that of the visual alert signal.

In such a system, the color of the visual alert signal may be related to an intensity of the current level of stress that the first responder is experiencing, and a patterning of the visual alert signal may be related to a duration of the current level of stress that the first responder is experiencing.

In another example, an alert system for monitoring physiological and/or environmental parameters that relate to a stress level experienced by a first responder, and issuing an alert as a function of the stress level, comprises an alerting device comprising an adapter module that is communicably coupled to an existing portable radio and an existing remote speaker/microphone, the adapter module including a light source for at least partially issuing the alert and a low-power radio transceiver for wirelessly receiving the physiological and/or environmental parameters from a wearable sensor worn by the first responder, and a stress management application in wireless communication with the adapter module, for customizing one or more settings and one or more personalized thresholds for the first responder related to the stress level experienced by the first responder for issuing the alert.

In such a system, issuing the alert may further comprise projecting a signal light from the light source, where a color of the signal light relates to an intensity of the stress level experienced by the first responder and where a blinking pattern of the signal light relates to a duration of the stress level experienced by the first responder.

In such a system, issuing the alert may further comprise, via the adapter module, synthesizing a voice announcement related to the stress level experienced by the first responder and communicating the voice announcement to the first responder via the existing remote speaker/microphone and transmitting the voice announcement over the existing portable radio.

In such a system, the adapter module may further comprise a transceiver for communicating the alert to a cloud-based server that stores data related to one or more alerts corresponding to the first responder or other first responders using the alert system, the cloud-based server in communication with the stress management application. The stress management application may rely on machine learning to refine the one or more settings and/or one or more personalized thresholds for the first responder or other first responders using the alert system.

In another example, a method for reducing a risk of sudden cardiac death in a first responder comprises via an alerting device communicably coupled to an existing portable radio worn by the first responder, retrieving one or more parameters related to an intensity of a current stress level and a duration of the current stress level of the first responder, issuing a visual alert via the alerting device corresponding to the intensity and the duration of the current stress level of the first responder, transmitting the intensity and the duration of the current stress level to a cloud-based server accessible via a stress management application, and composing a voice announcement based on the current stress level and the duration of the current stress level.

In such a method, the alerting device may comprise an adapter module that communicably couples an existing remote speaker/microphone to the existing portable radio, the adapter module including a single light source for issuing the visual alert.

In such a method, the alerting device may comprise a microphone/speaker module that replaces an existing remote speaker/microphone. The microphone/speaker module may include a plurality of light sources for issuing the visual alert.

In another example, an alerting device for warning of a potential adverse health event for a first responder comprises one or more signal lights, a radio interface connector for communicably coupling to a portable radio, a transceiver, and a processor. The processor may execute instructions to generate a visual alert with the one or more signal lights based on sensor data and personalized thresholds to create a pattern corresponding to a duration of a stress event.

In such an example, the device may further comprise an adapter remote speaker microphone connector. The radio interface connector may be on a first side of the device and the adapter remote speaker microphone connector may be on an opposing side of the device. The device may further comprise a body having a bottom surface wherein the signal lights are disposed on the bottom surface.

In such an example, the alerting device may further comprise a speaker and a microphone.

In such an example, the processor may further execute instructions to compose a voice announcement based on the sensor data and personalized thresholds.

In such an example, the transceiver may link the alerting device to a stress management application and the personalized thresholds may be received by the transceiver from a stress management application.

In such an example, the processor may further execute instructions to transmit the sensor data to a remote storage device.

In such an example, the transceiver may be a low-power radio transceiver for receipt of sensor data.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. An alert system for reducing a risk of an adverse health event for a first responder, comprising:
   a wearable sensor and an alerting device, the alerting device capable to receive real-time data from the wearable sensor, the alerting device communicably coupled to, and in direct contact with outsides of, a remote speaker/microphone connector and an existing portable radio worn by the first responder;
   wherein the alerting device issues a visual alert signal based on the real-time data received from the wearable sensor, the visual alert signal a function of one or more personalized thresholds related to a current level of stress that the first responder is experiencing, and wherein the alerting device harvests power from the existing portable radio.

2. The alert system of claim 1, wherein reducing the risk of the adverse health event further comprises reducing a risk of sudden cardiac death.

3. The alert system of claim 1, wherein the wearable sensor receives a collection of physiological data from the first responder; and
   wherein the one or more personalized thresholds are related to the physiological data.

4. The alert system of claim 1, wherein the wearable sensor receives a collection of environmental data from the first responder; and
   wherein the one or more personalized thresholds are related to the environmental data.

5. The alert system of claim 1, wherein the alerting device further comprises an adapter module that is sandwiched between the remote speaker/microphone connector communicably coupled to an existing remote speaker/microphone, and the existing portable radio.

6. The alert system of claim 5, wherein the adapter module includes a high-brightness light source for issuing the visual alert signal.

7. The alert system of claim 1, wherein the alerting device comprises a microphone/speaker module that replaces an existing remote speaker/microphone, where the microphone/speaker module is communicably coupled to the existing portable radio.

8. The alert system of claim 7, wherein the microphone/speaker module includes a first signal light, a second signal light, and a third signal light, wherein issuing the visual alert signal includes illuminating one of the first signal light, the second signal light, or the third signal light.

9. The alert system of claim 1, wherein the alerting device further comprises a transceiver for communicating the current level of stress that the first responder is experiencing to a cloud-based server.

10. The alert system of claim 1, further comprising a stress management application in wireless communication with the alerting device, wherein one or more settings of the alerting device, that include at least the one or more personalized thresholds, are set via the stress management application.

11. The alert system of claim 1, wherein the alerting device further comprises a status check actuator that, when actuated, results in synthesis of a voice announcement related to the current level of stress that the first responder is experiencing; and wherein the status check actuator is illuminated via a color of light different than that of the visual alert signal.

12. The alert system of claim 1, wherein a color of the visual alert signal is related to an intensity of the current level of stress that the first responder is experiencing; and
wherein a patterning of the visual alert signal is related to a duration of the current level of stress that the first responder is experiencing.

13. An alert system for monitoring physiological and/or environmental parameters that relate to a stress level experienced by a first responder, and issuing an alert as a function of the stress level, the alert system comprising:
an alerting device comprising an adapter module that is communicably coupled to and sandwiched between an existing portable radio and an existing remote speaker/microphone, the adapter module arranged entirely outside of the existing portable radio and the existing remote speaker/microphone and configured to harvest power from the existing portable radio, the adapter module including a light source for at least partially issuing the alert and a low-power radio transceiver for wirelessly receiving the physiological and/or environmental parameters from a wearable sensor worn by the first responder; and
a stress management application in wireless communication with the adapter module, for customizing one or more settings and one or more personalized thresholds for the first responder related to the stress level experienced by the first responder for issuing the alert.

14. The alert system of claim 13, wherein issuing the alert further comprises projecting a signal light from the light source, where a color of the signal light relates to an intensity of the stress level experienced by the first responder and where a blinking pattern of the signal light relates to a duration of the stress level experienced by the first responder.

15. The alert system of claim 13, wherein issuing the alert further comprises, via the adapter module, synthesizing a voice announcement related to the stress level experienced by the first responder and communicating the voice announcement to the first responder via the existing remote speaker/microphone and transmitting the voice announcement over the existing portable radio.

16. The alert system of claim 13, wherein the adapter module further comprises a transceiver for communicating the alert to a cloud-based server that stores data related to one or more alerts corresponding to the first responder or other first responders using the alert system, the cloud-based server in communication with the stress management application; and
wherein the stress management application relies on machine learning to refine the one or more settings and/or one or more personalized thresholds for the first responder or other first responders using the alert system.

17. A method for reducing a risk of sudden cardiac death in a first responder, comprising:
via an alerting device communicably coupled to an existing portable radio worn by the first responder, retrieving one or more parameters related to an intensity of a current stress level and a duration of the current stress level of the first responder, wherein the alerting device comprises an adapter module physically coupled to an outside of, and sandwiched between, the existing portable radio and a remote speaker/microphone connector, wherein the adapter module is configured to harvest power from the existing portable radio;
issuing a visual alert via the alerting device corresponding to the intensity and the duration of the current stress level of the first responder;
transmitting the intensity and the duration of the current stress level to a cloud-based server accessible via a stress management application; and
composing a voice announcement based on the intensity of the current stress level and the duration of the current stress level.

18. The method of claim 17, wherein the adapter module is communicably coupled to an existing remote speaker/microphone, the adapter module including a single light source for issuing the visual alert.

19. The method of claim 17, wherein the alerting device comprises a microphone/speaker module that replaces an existing remote speaker/microphone; and
wherein the microphone/speaker module includes a plurality of light sources for issuing the visual alert.

20. An alerting device for warning of a potential adverse health event for a first responder, comprising:
one or more signal lights;
an adapter module for communicably coupling to a portable radio;
a transceiver; and
a processor;
wherein the processor executes instructions to:
generate a visual alert signal with the one or more signal lights based on sensor data and personalized thresholds to create a pattern corresponding to a duration of a stress event, wherein the one or more signal lights are arranged on the adapter module physically coupled to an outside of, and configured to harvest power from, the portable radio.

21. The alerting device of claim 20, wherein the alerting device further comprises an adapter remote speaker/microphone connector.

22. The alerting device of claim 21, wherein the adapter module is physically coupled to the portable radio on a first side of the adapter module and the adapter remote speaker/microphone connector is physically coupled to a second side, opposite the first side, of the adapter module.

23. The alerting device of claim 21, wherein the adapter module comprises a bottom surface, and wherein the one or more signal lights are disposed on the bottom surface.

24. The alerting device of claim 20, wherein the alerting device further comprises a speaker and a microphone.

25. The alerting device of claim 20, wherein the processor further executes instructions to compose a voice announcement based on the sensor data and the personalized thresholds.

26. The alerting device of claim 20, wherein the transceiver links the alerting device to a stress management application, and wherein the personalized thresholds are received by the transceiver from the stress management application.

27. The alerting device of claim 20, wherein the processor further executes instructions to transmit the sensor data to a remote storage device.

28. The alerting device of claim 20, wherein the transceiver is a low-power radio transceiver for receipt of the sensor data.

* * * * *